US012414958B2

(12) United States Patent
Nowakowska et al.

(10) Patent No.: US 12,414,958 B2
(45) Date of Patent: Sep. 16, 2025

(54) MEDICAMENT AND USE THEREOF FOR TREATING BACTERIAL INFECTIONS INVOLVING BIOFILM

(71) Applicant: Debiopharm International S.A., Lausanne (CH)

(72) Inventors: Justyna Nowakowska, Sion (CH); Linda Kadi, Segny (FR); Grégoire Vuagniaux, Lausanne (CH)

(73) Assignee: Debiopharm International S.A., Lausanne (CH)

( * ) Notice: Subject to any disclaimer, the term of this patent is extended or adjusted under 35 U.S.C. 154(b) by 894 days.

(21) Appl. No.: 17/618,882

(22) PCT Filed: Jun. 12, 2020

(86) PCT No.: PCT/EP2020/066305
§ 371 (c)(1),
(2) Date: Dec. 13, 2021

(87) PCT Pub. No.: WO2020/249731
PCT Pub. Date: Dec. 17, 2020

(65) Prior Publication Data
US 2023/0126947 A1   Apr. 27, 2023

(30) Foreign Application Priority Data
Jun. 14, 2019  (EP) .................................... 19180281

(51) Int. Cl.
*A61K 31/675* (2006.01)
*A61K 9/70* (2006.01)
*A61K 35/74* (2015.01)
*A61K 45/06* (2006.01)
*A61P 31/04* (2006.01)

(52) U.S. Cl.
CPC .......... *A61K 31/675* (2013.01); *A61K 9/7007* (2013.01); *A61K 35/74* (2013.01); *A61K 45/06* (2013.01); *A61P 31/04* (2018.01)

(58) Field of Classification Search
None
See application file for complete search history.

(56) References Cited

U.S. PATENT DOCUMENTS

| | | | |
|---|---|---|---|
| 3,828,068 A | 8/1974 | Minieri |
| 4,154,943 A | 5/1979 | Kuehne |
| 4,977,159 A | 12/1990 | Sevrin et al. |
| 5,416,193 A | 5/1995 | Desai |
| 5,614,551 A | 3/1997 | Dick et al. |
| 5,624,941 A | 4/1997 | Barth et al. |
| 5,932,743 A | 8/1999 | Collini et al. |
| 5,985,867 A | 11/1999 | Rodgers et al. |
| 5,989,832 A | 11/1999 | Trias et al. |
| 6,133,260 A | 10/2000 | Matzke et al. |
| 6,174,878 B1 | 1/2001 | Gamache et al. |
| 6,184,380 B1 | 2/2001 | Chiu et al. |
| 6,187,341 B1 | 2/2001 | Johnson et al. |
| 6,194,429 B1 | 2/2001 | Guinn et al. |
| 6,194,441 B1 | 2/2001 | Roberts et al. |
| 6,198,000 B1 | 3/2001 | Hawkins |
| 6,221,859 B1 | 4/2001 | Dorso et al. |
| 6,221,864 B1 | 4/2001 | Hirayama et al. |
| 6,235,908 B1 | 5/2001 | Fey |
| 6,239,113 B1 | 5/2001 | Dawson et al. |
| 6,239,141 B1 | 5/2001 | Allen et al. |
| 6,248,363 B1 | 6/2001 | Patel et al. |
| 6,267,985 B1 | 7/2001 | Chen et al. |
| 6,277,836 B1 | 8/2001 | Borody |
| 6,288,239 B1 | 9/2001 | Hollingsworth et al. |
| 6,291,462 B1 | 9/2001 | Bartholomaeus et al. |
| 6,294,192 B1 | 9/2001 | Patel et al. |
| 6,303,572 B1 | 10/2001 | Rowe |
| 6,309,663 B1 | 10/2001 | Patel et al. |
| 6,333,045 B1 | 12/2001 | Yasueda et al. |
| 6,340,689 B1 | 1/2002 | Dubois et al. |
| 6,346,391 B1 | 2/2002 | Oethinger et al. |
| 6,367,985 B1 | 4/2002 | Lee et al. |
| 6,372,752 B1 | 4/2002 | Staveski et al. |
| 6,388,070 B1 | 5/2002 | Deshpande et al. |
| 6,395,746 B1 | 5/2002 | Caale et al. |
| 6,399,629 B1 | 6/2002 | Chamberland et al. |
| 6,406,880 B1 | 6/2002 | Thornton |
| 6,423,341 B1 | 7/2002 | Yamaguchi |
| 6,423,741 B1 | 7/2002 | Khanuja et al. |

(Continued)

FOREIGN PATENT DOCUMENTS

| | | | |
|---|---|---|---|
| CA | 2444597 A1 | 10/2002 |
| CA | 2568914 A1 | 12/2005 |

(Continued)

OTHER PUBLICATIONS

Hungarian Search Report mailed Dec. 31, 2003 for Hungarian Application No. P0203122.
International Search Report dated Sep. 12, 2007 for PCT/US2006/045903.
International Search Report dated Jun. 5, 2008 for PCT/CA2008/000300.
International Preliminary Report on Patentability mailed Jan. 20, 2009 for International Application No. PCT/CA2007/001277.
International Search Report and Written Opinion mailed Nov. 30, 2011 for International Application No. PCT/US2011/040187.
European Search Report mailed Oct. 30, 2013 for European Application No. 11793310.1.

(Continued)

*Primary Examiner* — Brian J Davis
(74) *Attorney, Agent, or Firm* — Wolf, Greenfield & Sacks, P.C.

(57) ABSTRACT

The present invention relates to the use of Afabicin in a method of treating bacterial infections involving biofilm that contains *staphylococcus* bacteria, wherein the method comprises administering Afabicin in combination with at least one further agent selected from lipopeptides, glycopeptides and lincosamides, such as Daptomycin and/or Vancomycin to the patient.

42 Claims, 3 Drawing Sheets

(56) References Cited

U.S. PATENT DOCUMENTS

| | | |
|---|---|---|
| 6,428,579 B1 | 8/2002 | Valentini |
| 6,432,444 B1 | 8/2002 | Fischetti et al. |
| 6,432,670 B1 | 8/2002 | Payne et al. |
| 6,436,980 B1 | 8/2002 | Leaer et al. |
| 6,441,162 B2 | 8/2002 | Yasui et al. |
| 6,448,054 B1 | 9/2002 | Poznansky et al. |
| 6,448,238 B1 | 9/2002 | Shoichet et al. |
| 6,448,449 B2 | 9/2002 | Larrow |
| 6,451,339 B2 | 9/2002 | Patel et al. |
| 6,451,816 B1 | 9/2002 | Biedermann et al. |
| 6,461,607 B1 | 10/2002 | Farmer |
| 6,461,829 B1 | 10/2002 | Kahne |
| 6,465,429 B1 | 10/2002 | Hancock et al. |
| 6,468,964 B1 | 10/2002 | Rowe |
| 6,469,046 B1 | 10/2002 | Daines et al. |
| 6,486,148 B2 | 11/2002 | Savage et al. |
| 6,486,149 B2 | 11/2002 | Onodera et al. |
| 6,486,165 B2 | 11/2002 | Zhang et al. |
| 6,489,318 B1 | 12/2002 | Copar et al. |
| 6,492,351 B1 | 12/2002 | Zhang et al. |
| 6,495,158 B1 | 12/2002 | Buseman et al. |
| 6,495,161 B1 | 12/2002 | Soon-Shiong et al. |
| 6,495,551 B1 | 12/2002 | Betts et al. |
| 6,497,886 B1 | 12/2002 | Breitenbach et al. |
| 6,500,459 B1 | 12/2002 | Chhabra et al. |
| 6,500,463 B1 | 12/2002 | van Lengerich |
| 6,503,539 B2 | 1/2003 | Gestrelius et al. |
| 6,503,881 B2 | 1/2003 | Krieger et al. |
| 6,503,903 B1 | 1/2003 | Miller et al. |
| 6,503,906 B1 | 1/2003 | Lee |
| 6,503,908 B1 | 1/2003 | Maw |
| 6,503,953 B2 | 1/2003 | Vyden |
| 6,503,955 B1 | 1/2003 | Dobrozsi et al. |
| 6,509,327 B1 | 1/2003 | Cagle et al. |
| 6,514,535 B2 | 2/2003 | Marchant |
| 6,514,541 B2 | 2/2003 | Khanuja et al. |
| 6,514,953 B1 | 2/2003 | Armitage et al. |
| 6,514,962 B1 | 2/2003 | Shibatani et al. |
| 6,514,986 B2 | 2/2003 | de Souza et al. |
| 6,515,113 B2 | 2/2003 | Raymond et al. |
| 6,517,827 B1 | 2/2003 | Bacon Kurtz et al. |
| 6,518,239 B1 | 2/2003 | Kuo et al. |
| 6,518,263 B1 | 2/2003 | Nishitani et al. |
| 6,518,270 B1 | 2/2003 | Amin et al. |
| 6,518,487 B1 | 2/2003 | Lowe et al. |
| 6,521,408 B1 | 2/2003 | Kawasaki |
| 6,525,066 B2 | 2/2003 | Fukumoto et al. |
| 6,527,759 B1 | 3/2003 | Tachibana et al. |
| 6,528,089 B1 | 3/2003 | Kothrade et al. |
| 6,531,126 B2 | 3/2003 | Farmer |
| 6,531,291 B1 | 3/2003 | Kabbash et al. |
| 6,531,465 B1 | 3/2003 | Ascher et al. |
| 6,531,508 B1 | 3/2003 | Nomura et al. |
| 6,531,649 B1 | 3/2003 | Mannerloef et al. |
| 6,559,172 B1 | 5/2003 | Heerding et al. |
| 6,573,272 B1 | 6/2003 | Miller et al. |
| 6,673,941 B2 | 1/2004 | Heerding et al. |
| 6,703,684 B2 | 3/2004 | Udrea et al. |
| 6,730,684 B1 | 5/2004 | Miller et al. |
| 6,762,201 B1 | 7/2004 | Miller et al. |
| 6,765,005 B2 | 7/2004 | Miller et al. |
| 6,821,746 B2 | 11/2004 | DeWolf, Jr. et al. |
| 6,846,819 B1 | 1/2005 | Miller et al. |
| 6,951,729 B1 | 10/2005 | Dewolf, Jr. et al. |
| 6,964,970 B2 | 11/2005 | Miller et al. |
| 6,995,254 B1 | 2/2006 | Payne et al. |
| 7,048,926 B2 | 5/2006 | Brandt et al. |
| 7,049,310 B2 | 5/2006 | Burgess et al. |
| 7,250,424 B2 | 7/2007 | Burgess et al. |
| 7,449,458 B2 | 11/2008 | Bhamidipati et al. |
| 7,524,843 B2 | 4/2009 | Miller et al. |
| 7,538,108 B2 | 5/2009 | Singh et al. |
| 7,557,125 B2 | 7/2009 | Miller et al. |
| 7,563,892 B1 | 7/2009 | Sinqh et al. |
| 7,741,339 B2 | 6/2010 | Burgess et al. |
| 7,790,709 B2 | 9/2010 | Berman et al. |
| 7,790,716 B2 | 9/2010 | Miller et al. |
| 7,879,872 B2 | 2/2011 | Berman et al. |
| 7,989,448 B2 | 8/2011 | Singh et al. |
| 8,003,673 B2 * | 8/2011 | Alder ............... A61P 31/00 514/359 |
| 8,153,652 B2 | 4/2012 | Burgess et al. |
| 8,163,902 B2 | 4/2012 | Bhamidipati et al. |
| 8,173,646 B2 | 5/2012 | Miller et al. |
| 8,211,888 B2 | 7/2012 | Singh et al. |
| 8,211,889 B2 | 7/2012 | Singh et al. |
| 8,263,613 B2 | 9/2012 | Pauls et al. |
| 8,318,720 B2 | 11/2012 | Pauls et al. |
| 8,450,307 B2 | 5/2013 | Sargent et al. |
| 8,741,855 B2 | 6/2014 | Quave et al. |
| 8,901,105 B2 | 12/2014 | Partridge et al. |
| 10,035,813 B2 | 7/2018 | Partridge et al. |
| 10,751,351 B2 | 8/2020 | Vuagniaux et al. |
| 2001/0016662 A1 | 8/2001 | Golik et al. |
| 2003/0232850 A1 | 12/2003 | Miller et al. |
| 2004/0053814 A1 | 3/2004 | Brandt et al. |
| 2004/0127403 A1 | 7/2004 | Parenti et al. |
| 2004/0147580 A1 | 7/2004 | Burgess et al. |
| 2005/0250810 A1 | 11/2005 | Miller et al. |
| 2006/0142265 A1 | 6/2006 | Berman et al. |
| 2006/0183908 A1 | 8/2006 | Berman et al. |
| 2006/0211657 A1 | 9/2006 | Singh et al. |
| 2006/0234983 A1 | 10/2006 | Singh et al. |
| 2008/0125423 A1 | 5/2008 | Miller et al. |
| 2009/0042927 A1 | 2/2009 | Pauls et al. |
| 2009/0156578 A1 | 6/2009 | Pauls et al. |
| 2009/0221699 A1 | 9/2009 | Burgess et al. |
| 2010/0130470 A1 | 5/2010 | Pauls et al. |
| 2011/0124633 A1 | 5/2011 | Berman et al. |
| 2012/0010127 A1 | 1/2012 | Berman et al. |
| 2013/0237523 A1 | 9/2013 | Pauls et al. |
| 2013/0281442 A1 | 10/2013 | Hafkin |
| 2014/0051666 A1 | 2/2014 | Partridge et al. |
| 2014/0107106 A1 | 4/2014 | Sargent et al. |
| 2015/0065415 A1 | 3/2015 | Partridge et al. |
| 2019/0054100 A1 | 2/2019 | Vuagniaux et al. |
| 2022/0142993 A1 | 5/2022 | Decrette et al. |

FOREIGN PATENT DOCUMENTS

| | | |
|---|---|---|
| CA | 2776849 A1 | 5/2011 |
| CN | 101415701 A | 4/2009 |
| CN | 102675311 A | 9/2012 |
| CN | 104684922 A | 6/2015 |
| CN | 108778286 A | 11/2018 |
| EP | 0407200 A1 | 1/1991 |
| EP | 0953570 A1 | 11/1999 |
| EP | 1000935 A1 | 5/2000 |
| EP | 3923914 A1 | 12/2021 |
| HU | 0203122 B | 5/1991 |
| HU | 210679 B | 6/1995 |
| JP | 11-302173 A | 11/1999 |
| JP | 2005-519984 A | 7/2005 |
| JP | 2015-521617 A | 7/2015 |
| JP | 2019-512467 A | 5/2019 |
| WO | WO 93/04035 A1 | 3/1993 |
| WO | WO 95/18619 A1 | 7/1995 |
| WO | WO 96/00730 A1 | 1/1996 |
| WO | WO 97/48696 A1 | 12/1997 |
| WO | WO 98/57952 A1 | 12/1998 |
| WO | WO 99/24406 A1 | 5/1999 |
| WO | WO 00/27628 A1 | 5/2000 |
| WO | WO 00/57933 A1 | 10/2000 |
| WO | WO 01/26652 A1 | 4/2001 |
| WO | WO 01/26654 A1 | 4/2001 |
| WO | WO 01/27103 A1 | 4/2001 |
| WO | WO 01/41573 A1 | 6/2001 |
| WO | WO 01/48248 A2 | 7/2001 |
| WO | WO 01/70172 A2 | 9/2001 |
| WO | WO 02/10332 A1 | 2/2002 |
| WO | WO 02/42273 A2 | 5/2002 |
| WO | WO 02/48097 A1 | 6/2002 |
| WO | WO 02/064572 A1 | 8/2002 |
| WO | WO 03/086396 A1 | 10/2003 |

(56) References Cited

FOREIGN PATENT DOCUMENTS

| | | |
|---|---|---|
| WO | WO 03/088897 A2 | 10/2003 |
| WO | WO 2004/014869 A2 | 2/2004 |
| WO | WO 2004/052890 A1 | 6/2004 |
| WO | WO 2004/082586 A2 | 9/2004 |
| WO | WO 2005/090367 A1 | 9/2005 |
| WO | WO 2006/130629 A2 | 12/2006 |
| WO | WO 2007/053131 A2 | 5/2007 |
| WO | WO 2007/067416 A2 | 6/2007 |
| WO | WO 2008/009122 A1 | 1/2008 |
| WO | WO 2008/064274 A1 | 5/2008 |
| WO | WO 2008/098374 A1 | 8/2008 |
| WO | WO 2009/003136 A1 | 12/2008 |
| WO | WO 2010/0151689 A1 | 12/2010 |
| WO | WO 2010/151711 A1 | 12/2010 |
| WO | WO 2011/002999 A1 | 1/2011 |
| WO | WO 2011/061214 A1 | 5/2011 |
| WO | WO 2011/156811 A2 | 12/2011 |
| WO | WO 2013/080222 A1 | 6/2013 |
| WO | WO 2013/190384 A1 | 12/2013 |
| WO | WO 2015/118496 A1 | 8/2015 |
| WO | WO 2017/144717 A1 | 8/2017 |
| WO | WO 2020/249731 A1 | 12/2020 |

OTHER PUBLICATIONS

International Search Report and Written Opinion mailed Dec. 3, 2013 for International Application No. PCT/IB2013/001780.
European Search Report dated Jul. 16, 2014 for European Application No. 08714623.9.
International Search Report and Written Opinion mailed May 26, 2017 for International Application No. PCT/EP2017/054470.
International Search Report and Written Opinion mailed Apr. 1, 2020 for International Application No. PCT/EP2020/053882.
International Preliminary Report on Patentability mailed Aug. 26, 2021 for International Application No. PCT/EP2020/053882.
International Search Report and Written Opinion mailed Oct. 6, 2020 for International Application No. PCT/EP2020/066305.
International Preliminary Report on Patentability mailed Dec. 14, 2021 for International Application No. PCT/EP2020/066305.
Abou-Gharbia et al., Psychotropic agents: synthesis and antipsychotic activity of substituted beta-carbolines. J Med Chem. Jun. 1987;30(6):1100-5. doi: 10.1021/jm00389a022.
Ahsan et al. Reserpine analogues: synthesis of β-carboline derivative. J. Chem. Soc. 1963:3928-30. doi: 10.1039/JR9630003928.
Annesley et al., Glucuronidation of prodrug reactive site: isolation and characterization of oxymethylglucuronide metabolite of fosphenytoin. Clin Chem. May 2001;47(5):910-8.
Arakawa et al., Biotechnology applications of amino acids in protein purification and formulations. Amino Acids. Nov. 2007;33(4):587-605. doi: 10.1007/s00726-007-0506-3. Epub Mar. 16, 2007.
Arora et al., Cutaneous microcirculation in the neuropathic diabetic foot improves significantly but not completely after successful lower extremity revascularization. J Vasc Surg. Mar. 2002;35(3):501-5.
Banu et al., Spectrum of bacteria associated with diabetic foot ulcer and biofilm formation: A prospective study. Australas Med J. Sep. 30, 2015;8(9):280-5. doi: 10.4066/AMJ.2015.2422. eCollection 2015.
Barkema et al., Invited Review: The role of cow, pathogen, and treatment regimen in the therapeutic success of bovine *Staphylococcus aureus* mastitis. J Dairy Sci. Jun. 2006;89(6):1877-95. doi: 10.3168/jds.S0022-0302(06)72256-1.
Bastin et al., Salt Selection and Optimisation Procedure for Pharmaceutical New Chemical Entities, Organic Process Res. & Dev., 2000;4(5):427-35.
Berge et al., Pharmaceuticals Salts, J. of Pharm. Sciences, 1977;66(1):1-19.
Bergler et al., Protein EnvM is the NADH-dependent enoyl-ACP reductase (FabI) of *Escherichia coli*. J Biol Chem. Feb. 25, 1994;269(8):5493-6.

Boffeli et al., In-office distal Symes lesser toe amputation: a safe, reliable, and cost-effective treatment of diabetes-related tip of toe ulcers complicated by osteomyelitis. J Foot Ankle Surg. Nov.-Dec. 2014;53(6):720-6. doi: 10.1053/j.jfas.2014.04.020. Epub Jul. 22, 2014.
Chen et al., Synthesis and antibacterial evaluation of certain quinolone derivatives. J Med Chem. Jul. 5, 2001;44(14):2374-7. doi: 10.1021/jm0100335.
Claus et al., Formaldehydabspaltende Phenolcarbonsaurederivte Monatsh. Chem. 1966;97:271-9.
Database CA on STN, AN 7:66733, Rosenmund et al., "Chemistry of indole II. Beckmann and Schmidt Rearran ements of Some Indole Ketones," Chem. Ber., 103 2: 496-509 1970.
Database CAOLD on STN, AN CA51:10524d, Hellman et al., "N-Mannich bases (VI) condensation of N-dialkylaminomethylbenzamides with amines and amides, (VII) N-acylaminomethylation of indole," Direct Submission, 1953.
Database CAPLUS on STN AN 1999:325910 Aslanian, et al., "Preparation of (phenvlaikv)imidazoles as H3 receptor antagonists," W099/24406. 1999.
Database CAPLUS on STN, AN 1977:439214. Misztal et al., "Synthesis and pharmacologic properties of pyridoyl derivatives of 3-methylaminoindole 2-methyltryptamine and isotryptamine," Arch Immuno Ther Exp., 24(6):851-862, 1976.
Database CAPLUS on STN, AN 1986:68547, Stuetz et al., "Synthesis and Structure-activity relationships of naftifine-related allvlamine antimycotics," J. Med. Chem., 29(1):112-25, 1986.
Database CAPLUS on STN, AN 1991:428908, Fuse et al., "Preparation of cinnamamide derivatives an antihyperlipidemics," EP407200A1, 1991.
Database Crossfile Beilstein, 1966, Database accession No. 2819049, 2819050, XP002216033.
Dykhuizen, Santa Rosalia revisited: why are there so many species of bacteria? Antonie Van Leeuwenhoek. Jan. 1998;73(1):25-33. doi: 10.1023/a:1000665216662.
Ettmayer et al., Lessons learned from marketed and investigational prodrugs. J Med Chem. May 6, 2004;47(10):2393-404. doi: 10.1021/jm0303812.
Foroumadi et al., Synthesis and in vitro antibacterial evaluation of N-[5-(5-nitro-2-thienyl)-1,3,4-thiadiazole-2-yl] piperazinyl quinolones. Eur J Med Chem. Sep. 2003;38(9):851-4. doi: 10.1016/s0223-5234(03)00148-x.
"Gokarn et al., Amino Acids. In: Excipient Development for Pharmaceutical, Biotechnology, and Drug Delivery Systems. 2006. Katdare et al., Eds. pp. 299-300."
Grassberger et al., Preparation and antibacterial activities of new 1,2,3-diazaborine derivatives and analogues. J Med Chem. Aug. 1984;27(8):947-53. doi: 10.1021/jm00374a003.
Heath et al., A triclosan-resistant bacterial enzyme. Nature. Jul. 13, 2000;406(6792): 145-6. doi: 10.1038/35018162. Erratum in: Nature Aug. 24, 2000;406(6798):848.
Heath et al., Regulation of fatty acid elongation and initiation by acyl-acyl carrier protein in *Escherichia coli*. J Biol Chem. Jan. 26, 1996;271(4):1833-6. doi: 10.1074/jbc.271.4.1833.
Heck, Palladium-Catalyzed Vinylation of Organic Halides. Organic Reactions. 1982;27:345-90. doi: http://dx.doi.org./10.1002/0471264180.or027.02.
Heimbach et al., Absorption rate limit considerations for oral phosphate prodrugs. Pharm Res. Jun. 2003;20(6):848-56. doi: 10.1023/a:1023827017224.
Hill et al., The Effects of Peripheral Vascular Disease with Osteomyelitis in the Diabetic Foot. Am. J. Surg. Apr. 1999;177:282-6.
Himmler et al., Synthesis and antibacterial in vitro activity of novel analogues of nematophin. Bioorg Med Chem Lett. Aug. 4, 1998;8(15):2045-50. doi: 10.1016/s0960-894x(98)00358-8.
Jossang-Yanagida et al., Tetrahydropyridoazepines and Tetrahydropyridoazepinones from the Corresponding Dihydroquinolones. J. Heterocyclic Chemistry. Mar. 1978;15(2):249-51. doi: 10.1002/jhet.5570150213.
Kaplan et al., Abstract F1-2005 "In Vitro and In Vivo Absorption Properties of AFN-1252, a Novel Specific-Spectrum Anti-Staphylcoccal Agent," American Society for Microbiology 49th ICAAC Meeting Abstract, Tuesday, Sep. 15, 2009.

(56) References Cited

OTHER PUBLICATIONS

Kaplan et al., Abstract F1-2006 "Correlation of AFN-1252 Phase 0 Microdosing and Phase 1 Pharmacokinetics" American Society for Microbiology 49th ICAAC Meeting Abstract, Tuesday, Sep. 15, 2009.
Kaplan et al., In vitro activity (MICs and rate of kill) of AFN-1252, a novel FabI inhibitor, in the presence of serum and in combination with other antibiotics. J Chemother. Feb. 2013;25(1):18-25. doi: 10.1179/1973947812Y.0000000063.
Karchmer et al., Is there a future for FabI inhibitors as antibacterial agents? Clin. Invest. 2013;3(8):707-9.
Karlowsky et al., AFN-1252, a FabI inhibitor, demonstrates a *Staphylococcus*-specific spectrum of activity. Antimicrob Agents Chemother. Aug. 2009;53(8):3544-8. doi: 10.1128/AAC.00400-09. Epub Jun. 1, 2009.
Karlowsky et al., In vitro activity of API-1252, a novel FabI inhibitor, against clinical isolates of *Staphylococcus aureus* and *Staphylococcus epidermidis*. Antimicrob Agents Chemother. Apr. 2007;51(4):1580-1. doi: 10.1128/AAC.01254-06. Epub Jan. 12, 2007.
Kearney et al., The in vitro enzymic labilities of chemically distinct phosphomonoester prodrugs. Pharm Res. Apr. 1992;9(4):497-503. doi: 10.1023/a:1015840329786.
Lakemeyer et al., Thinking Outside the Box-Novel Antibacterials to Tackle the Resistance Crisis. Angew Chem Int Ed Engl. Oct. 26, 2018;57(44):14440-14475. doi: 10.1002/anie.201804971. Epub Oct. 11, 2018.
Leppik et al., Pharmacokinetics and safety of a phenytoin prodrug given i.v. or i.m. in patients. Neurology. Mar. 1990;40(3 Pt 1):456-60. doi: 10.1212/wnl.40.3_part_1.456.
Levy et al., Molecular basis of triclosan activity. Nature. Apr. 1, 1999;398(6726):383-4. doi: 10.1038/18803.
Li et al., Synthesis and Antistatphyloccocal Activity of Nematophin and its Analogs, Bioorganic & Medicinal Chemistry Letters Oxford, GB, May 20, 1997;7(10):1349-1352.
Lipsky et al., Treating diabetic foot osteomyelitis primarily with surgery or antibiotics: have we answered the question? Diabetes Care. 2014;37(3):593-5. doi: 10.2337/dc13-2510.
McMurry et al., Triclosan targets lipid synthesis. Nature. Aug. 6, 1998;394(6693):531-2. doi: 10.1038/28970.
Menetrey et al., Bone and Joint Tissue Penetration of the *Staphylococcus*-Selective Antibiotic Afabicin in Patients Undergoing Elective Hip Replacement Surgery. Antimicrob Agents Chemother. Feb. 26, 2019;63(3):e01669-18. doi: 10.1128/AAC.01669-18.
Menetrey et al., Mass Balance, Pharmacokinetics and Metabolism of the Antimicrobial Afabicin Following Intravenous and Oral Administration in Humans. Clin Ther. Aug. 1, 2017;39(8):E65. doi: 10.1016/j.clinthera.2017.05.200.
Miller et al., Discovery of aminopyridine-based inhibitors of bacterial enoyl-ACP reductase (FabI). J Med Chem. Jul. 18, 2002;45(15):3246-56. doi: 10.1021/jm020050+.
Misztal et al., Synthesis and pharmacologic properties of pyridoyl derivatives of 3-methylaminoindole 2-methyltryptamine and isotryptamine. Arch Immunol Ther Exp (Warsz). 1976;24(6):851-62.
Nicolau et al., Therapeutic options for diabetic foot infections: a review with an emphasis on tissue penetration characteristics. J Am Podiatr Med Assoc. Jan.-Feb. 2010;100(1):52-63. Review.
Pachter et al., The Chemistry of Hortiamine and 6-Methoxyhetsinine. J. Amer. Chem. Feb. 1961;83(3):635-42. doi: 10.1021/ja01464a032.
Payne et al., Bacterial fatty-acid biosynthesis: a genomics-driven target for antibacterial drug discovery. Drug Discov Today. May 1, 2001;6(10):537-544. doi: 10.1016/s1359-6446(01)01774-3.
Payne et al., Discovery of a novel and potent class of FabI-directed antibacterial agents. Antimicrob Agents Chemother. Oct. 2002;46(10):3118-24. doi: 10.1128/AAC.46.10.3118-3124.2002.
Pee et al., A FASII Inhibitor Prevents Staphylococcal Evasion of Daptomycin by Inhibiting Phospholipid Decoy Production. Antimicrob Agents Chemother. Mar. 27, 2019;63(4):e02105-18. doi: 10.1128/AAC.02105-18.

Ramnauth et al., 2,3,4,5-Tetrahydro-1H-pyrido[2,3-b and e][1,4]diazepines as inhibitors of the bacterial enoyl ACP reductase, FabI. Bioorg Med Chem Lett. Sep. 15, 2009;19(18):5359-62. doi: 10.1016/j.bmcl.2009.07.094. Epub Jul. 23, 2009.
Rautio et al., Prodrugs: design and clinical applications. Nat Rev Drug Discov. Mar. 2008;7(3):255-70. doi: 10.1038/nrd2468. Erratum in: Nat Rev Drug Discov. Mar. 2008;7(3):272.
Rautio et al., Prodrugs—Recent approvals and a glimpse of the pipeline. Eur J Pharm Sci. Nov. 15, 2017;109:146-161. doi: 10.1016/j.ejps.2017.08.002. Epub Aug. 4, 2017.
Rehse et al., Dopaminanaloge 1,2,3,4-Tetrahydro-beta-carboline [Dopamine analogous 1,2,3,4-tetrahydro-beta-carbolines (author's transl)]. Arch Pharm (Weinheim). Jan. 1978;311(1):11-8. German. doi: 10.1002/ardp.19783110104.
Saginur et al., Multiple combination bactericidal testing of staphylococcal biofilms from implant-associated infections. Antimicrob Agents Chemother. Jan. 2006;50(1):55-61. doi: 10.1128/AAC.50.1.55-61.2006.
Seefeld et al., Indole naphthyridinones as inhibitors of bacterial enoyl-ACP reductases FabI and FabK. J Med Chem. Apr. 24, 2003;46(9):1627-35. doi: 10.1021/jm0204035.
Shoji et al., Two Novel Alkaloids from Evodia rutaecarpa. J. Nat. Prod. 1989;52(5):1160-2. doi: 10.1021/np50065a043.
Sladowska et al., Synthesis and properties of amides of 1-benzyl-3-methyl- and 1-butyl-3-phenyl-7-methyl-4-oxo-2-thioxo (2,4-dioxo)-1,2,3,4-tetrahydropyrido-[2,3-d]pyrimidine-6-carboxylic acids. Farmaco Sci. Dec. 1986;41(12):954-63.
Stutz et al., Synthesis and structure-activity relationships of naftifine-related allylamine antimycotics. J Med Chem. Jan. 1986;29(1):112-25. doi: 10.1021/jm00151a019.
Turnowsky et al., envM genes of *Salmonella typhimurium* and *Escherichia coli*. J Bacteriol. Dec. 1989;171(12):6555-65. doi: 10.1128/jb.171.12.6555-6565.1989.
Varia et al., Phenytoin prodrugs III: water-soluble prodrugs for oral and/or parenteral use. J Pharm Sci. Aug. 1984;73(8):1068-73. doi: 10.1002/jps.2600730812.
Varia et al., Phenytoin prodrugs IV: Hydrolysis of various 3-(hydroxymethyl)phenytoin esters. J Pharm Sci. Aug. 1984;73(8):1074-80. doi: 10.1002/jps.2600730813.
Varia et al., Phenytoin prodrugs V: In vivo evaluation of some water-soluble phenytoin prodrugs in dogs. J Pharm Sci. Aug. 1984;73(8):1080-7. doi: 10.1002/jps.2600730814.
Varia et al., Phenytoin prodrugs VI: In vivo evaluation of a phosphate ester prodrug of phenytoin after parenteral administration to rats. J Pharm Sci. Aug. 1984;73(8):1087-90. doi: 10.1002/jps.2600730815.
Ward et al., Kinetic and structural characteristics of the inhibition of enoyl (acyl carrier protein) reductase by triclosan. Biochemistry. Sep. 21, 1999;38(38):12514-25. doi: 10.1021/bi9907779.
Weiss et al., Efficacy of AFN-1252 and Vancomycin in the Mouse Subcutaneous Abscess Model with Methicillin-Resistant *Staphylococcus aureus*. Interscience Conference on Antimicrobial Agents & Chemotherapy (ICAAC). Jan. 2008;48:277. Abstract, 1 page.
HU P0203122, Dec. 31, 2003, Hungarian Search Report.
PCT/US2006/045903, Sep. 12, 2007, International Search Report.
PCT/CA2008/000300, Jun. 5, 2008, International Search Report.
PCT/CA2007/001277, Jan. 20, 2009, International Preliminary Report on Patentability.
PCT/US2011/040187, Nov. 30, 2011, International Search Report and Written Opinion.
EP 11793310.1, Oct. 30, 2013, European Search Report.
PCT/IB2013/001780, Dec. 3, 2013, International Search Report and Written Opinion.
EP 8714623.9, Jul. 16, 2014, European Search Report.
PCT/EP2017/054470, May 26, 2017, International Search Report and Written Opinion.
PCT/EP2020/053882, Apr. 1, 2020, International Search Report and Written Opinion.
PCT/EP2020/053882, Aug. 26, 2021, International Preliminary Report on Patentability.
PCT/EP2020/066305, Oct. 6, 2020, International Search Report and Written Opinion.

(56) References Cited

OTHER PUBLICATIONS

PCT/EP2020/066305, Dec. 14, 2021, International Preliminary Report on Patentability.
U.S. Appl. No. 14/010,166, filed Aug. 26, 2013, Partridge et al.
U.S. Appl. No. 14/534,573, filed Nov. 6, 2014, Partridge et al.
U.S. Appl. No. 16/079,804, filed Aug. 24, 2018, Vuagniaux et al.
U.S. Appl. No. 17/430,616, filed Aug. 12, 2021, Decrette et al.
Archer et al., *Staphylococcus aureus* biofilms: properties, regulation, and roles in human disease. Virulence. Sep.-Oct. 2011;2(5):445-59. doi: 10.4161/viru.2.5.17724. Epub Sep. 1, 2011.
Defres et al., MRSA as a cause of lung infection including airway infection, community-acquired pneumonia and hospital-acquired pneumonia. Eur Respir J. Dec. 2009;34(6):1470-6. doi: 10.1183/09031936.00122309.
Flamm et al., Activity of Debio1452, a FabI inhibitor with potent activity against *Staphylococcus aureus* and coagulase-negative *Staphylococcus* spp., including multidrug-resistant strains. Antimicrob Agents Chemother. May 2015;59(5):2583-7. doi: 10.1128/AAC.05119-14. Epub Feb. 17, 2015.
Huang et al., Amino acids as co-amorphous excipients for tackling the poor aqueous solubility of valsartan. Pharm Dev Technol. Feb. 2017;22(1):69-76. doi: 10.3109/10837450.2016.1163390. Epub Apr. 6, 2016.
Lovati et al., Does $PGE_1$ vasodilator prevent orthopaedic implant-related infection in diabetes? Preliminary results in a mouse model. PLoS One. Apr. 9, 2014;9(4):e94758. doi: 10.1371/journal.pone.0094758.
Maiden et al., Triclosan depletes the membrane potential in Pseudomonas aeruginosa biofilms inhibiting aminoglycoside induced adaptive resistance. PLoS Pathog. Oct. 30, 2020;16(10):e1008529. doi: 10.1371/journal.ppat.1008529.
Maiden et al., Triclosan Is an Aminoglycoside Adjuvant for Eradication of Pseudomonas aeruginosa Biofilms. Antimicrob Agents Chemother. May 25, 2018;62(6):e00146-18. doi: 10.1128/AAC.00146-18.
Müller et al., Prodrug approaches for enhancing the bioavailability of drugs with low solubility. Chem Biodivers. Nov. 2009;6(11):2071-83. doi: 10.1002/cbdv.200900114.
Yang et al., The influence of amino acids on aztreonam spray-dried powders for inhalation. Asian J Pharma Sci. Dec. 2015;10(6):541-548. doi: 10.1016/j.ajps.2015.08.002.
Huang et al., Comparison of the effects of human β-defensin 3, vancomycin, and clindamycin on *Staphylococcus aureus* biofilm formation. Orthopedics. Jan. 16, 2012;35(1):e53-60. doi: 10.3928/01477447-20111122-11.
Piechota et al., Biofilm Formation by Methicillin-Resistant and Methicillin-Sensitive *Staphylococcus aureus* Strains from Hospitalized Patients in Poland. Biomed Res Int. Dec. 27, 2018;2018:4657396. doi: 10.1155/2018/4657396.

\* cited by examiner

Zimmerli W et al. Orthopedic Implant-Associated Infections. In: Bennett J et al. eds. Mandell, Douglas, and Bennett's Principles and Practice of Infectious Diseases, Vol 1. 8th ed. Philadelphia, PA; Elsevier 2015

*Microbiologic sampling

+ Continuation with the same antibiotic regimen

Zimmerli W et al. 2015

MEDICAMENT AND USE THEREOF FOR TREATING BACTERIAL INFECTIONS INVOLVING BIOFILM

1. CROSS REFERENCE TO RELATED APPLICATION(S)

This Application is a National Stage filing under 35 U.S.C. 371 of International PCT Application No. PCT/EP2020/066305, filed Jun. 12, 2020, which claims priority to European Application Number 19180281.8, filed Jun. 14, 2019. The entire contents of these applications are incorporated herein by reference in their entirety.

2. TECHNICAL FIELD

The present invention relates to treatments of bacterial infections. More specifically, the present invention provides means and methods for treating bacterial infections, wherein the bacteria are organized in biofilms and preferably biofilms containing or consisting of *staphylococcus* bacteria. To accomplish the desired treatment effect, the present invention relies on a combination of Afabicin and at least one further antibiotic agent selected from the group consisting of lipopeptides, glycopeptides and lincosamides or a combination thereof.

3. BACKGROUND OF THE INVENTION

Bacteria may survive in the human body in isolated form, which is sometimes called a planktonic state. However, bacteria may also form biofilms, i.e. communities of cellular clusters attached typically to a solid native or foreign surface such as dental material, medical implants e.g. prosthetic joints, or the like. There is some degree of organization within biofilms including the formation of water channels as a circulatory system for the delivery of nutrients and removal of metabolic waste products. Moreover, the bacteria are embedded in an extracellular matrix that is typically composed of polysaccharides, proteins, teichoic acids, lipids and extracellular DNA.

The human immune system is typically not able to successfully eradicate such biofilm-mediated infections and, bacterial infections involving biofilms are notoriously difficult to treat, with most antibiotic drugs effective in the treatment of bacteria in the planktonic state not showing efficacy against biofilm-mediated infections of the same bacteria. This is believed to be caused by a combination of different defense mechanisms of biofilm-embedded bacteria, such as:

The extracellular matrix prevents or hinders access of the drug substance to the bacteria;
  At least some of the bacteria organized in biofilm are believed to be in a slow or non-growing state in which little or no extracellular materials are incorporated into the cell;
  Biofilms are believed to contain different bacterial sub-populations with different levels of resistance; this improves the chances that at least some sub-populations of the biofilm survive an antibiotic drug attack;
  The cells within biofilm may also rely on other defense mechanisms such as overexpression of certain genes and stress responses to hostile environmental conditions. Such other defense mechanisms may also vary within different sub-populations of the biofilm.

Accordingly, at present, there are only very limited treatment options available for biofilm-mediated bacterial infections. The current standard of care of anti-biofilm therapy relies on Rifampicin as the corner stone. However, the use of rifampicin is hindered by its toxicity and patient intolerance. Further, Rifampicin monotherapy frequently leads to induction of bacterial resistance, which renders the therapy ineffective and can leave patients with suboptimal or no treatment options. In addition, treatment of infection due to rifampicin-resistant *staphylococcus* involves also a change in surgical procedure to a more complex and longer strategy.

Rifampicin resistance rates in staphylococci differ between patient populations and countries. According to 2016 data from the European Committee on Antimicrobial Susceptibility Testing, the rates range from 0.5-17%. However, at least in some countries, including Belarus, Montenegro, Serbia and Turkey, levels of Rifampicin resistance in invasive *S. aureus* clinical isolates have reached 14-24%. Moreover, rifampicin intolerance and toxicity together with resistance can account for up to 25% of all acute staphylococcal prosthetic joint infections and resistance to rifampicin in *S. epidermidis* isolated from medical implant infections, more specifically prosthetic join infections, can amount to up to 39%.

Coagulase-negative staphylococci (CoNS), and especially *S. epidermidis*, the most frequent commensal of human epithelial surfaces, have emerged as important opportunistic pathogens. *S. epidermidis* is currently the main pathogen in catheter-related bloodstream infections and early-onset neonatal sepsis. It is also a frequent cause of biomedical device-related infections. The treatment challenge of these infections has been increasingly recognized, as a vast majority of nosocomial *S. epidermidis* infections can manifest with multidrug-resistance (e.g. resistance to beta-lactams, fluoroquinolones and rifampicin) and can be chronic in nature due to their biofilm formation.

In order to reduce the risk of rifampicin resistance induction, especially in the setting of biofilm-mediated infections associated with medical implants, the standard of care treatments rely on drug combinations involving Rifampicin and a second antibiotic drug. The second antibiotic drug is typically selected from Nafcillin, Oxacillin, Cefazolin, Vancomycin, Daptomycin, Linezolid, Ciprofloxacin, Levofloxacin, Co-trimoxazole, Minocycline, Doxycycline, oral first generation Cephalosphorins such as Cephalexin or anti-staphylococcal Penicillins such as Dicloxacillin, Clindamycin, Teicoplanin or fusidic acid. However, since rifampicin and these second antibiotics are associated with specific toxicities, the currently used combination therapy with Rifampicin can lead to cumulative adverse events.

In addition, it is recommended against the use of Rifampicin perioperatively (pre, during or post an operation), when the wounds are still wet or the drains are not yet removed, as well as when another surgery is planned. This is due to the risk of inducing resistance to Rifampicin in commensal bacteria, including staphylococci residing on the skin. Due to the proximity to open wounds and drainages these rifampicin-resistant staphylococci can cause superinfection of the medical implants. Delaying the use of Rifampicin to minimize this risk, may imply initial sub-optimal patient treatment.

Given the increasing limitations of Rifampicin outlined above, there is an urgent need for providing alternative treatments for biofilm-mediated infections that do not rely on Rifampicin. It is, therefore, an object of the present invention to provide such means and methods for treating biofilm-mediated bacterial infections, and especially biofilm-mediated infections involving *staphylococcus* bacteria, which do not rely on Rifampicin as a drug substance.

It is a further object of the present invention to provide means and methods for treating biofilm infections and preferably biofilm infections involving *staphylococcus* bacteria, which show cure rates of ≥ 20%, ≥25%, ≥30%, ≥35%, or ≥40% for infections involving young (24 h) biofilm and cure rates of ≥5%, ≥10%, or ≥15% for old (72 h) biofilm. It is well within the remit of the person skilled in the art to determine the cure rate of any means or method. In particular the cure rate may be determined using one or more of the models and techniques described in the Examples included herein.

Another objective of the present invention is to provide means and methods for treating biofilm infections and preferably biofilm infections involving *staphylococcus* bacteria, which can be used in patients with wet wounds, inserted drainages or planned surgeries (e.g. perioperatively).

Another objective of the present invention is to provide means and methods for treating biofilm infections and preferably biofilm infections involving *staphylococcus* bacteria, which can be used in cases in which rifampicin-based treatments are not feasible for reasons including but not limited to resistance or patient intolerance.

Further objectives underlying the present invention will become apparent in the detailed description provided below.

4. SUMMARY OF THE INVENTION

The present invention accomplishes the above objectives by providing combination therapies for the treatment of biofilm-mediated bacterial infections and preferably biofilm infections involving *staphylococcus* bacteria, which rely on a combination of Afabicin and at least one further antibiotic agent selected from the group consisting of lipopeptides, glycopeptides and lincosamides as the essential active pharmaceutical ingredients. The at least one further agent is preferably at least one agent selected from the group consisting of Daptomycin, Vancomycin, Surfactin, A54145, Amphomycin, Friulimicin, Iaspartomycin, WAP-8294A2, Katanosin, Plusbacin A3, Oritavancin, Telavancin, Teicoplanin, Dalbavancin, Ramoplanin, Mannopeptimycin, Clindamycin, Lincomycin and Pirlimycin, more preferably Daptomycin and/or Vancomycin and/or Clindamycin. It is also possible to employ a combination of Afabicin with two or more of these antibiotic agents. For instance, a combination of three antibiotics Afabicin, Daptomycin and Vancomycin or a combination of Afabicin, Daptomycin and Clindamycin or a combination of Afabicin, Vancomycin and Clindamycin may be used. For the sake of simplicity, the following description refers to these embodiments of the present invention jointly as "combination of Afabicin with at least one further agent" or the like. The present invention thus specifically relates to Afabicin for use in combination with Daptomycin and/or Vancomycin and/or Clindamycin (and vice versa) for the treatment of biofilm-mediated infections and preferably *staphylococcus*-containing biofilm-mediated infections. More specifically, the present invention relates to the following embodiments:

1. Afabicin for use in a method of treating bacterial infections involving biofilm wherein the method comprises administering Afabicin in combination with at least one further agent selected from the group consisting of lipopeptides, glycopeptides and lincosamides to the patient, wherein the lipopeptde is preferably Daptomycin, the glycopeptide is preferably Vancomycin and the lincosamide is preferably Clindamycin.

2. Afabicin for use according to item 1, wherein the biofilm contains or consists of *staphylococcus* bacteria.

3. Afabicin for use according to any one of items 1 to 2, wherein the *staphylococcus* bacteria are selected from the group consisting of:
    *Staphylococcus aureus*, including community-acquired *Staphylococcus aureus*, and hospital-acquired *Staphylococcus aureus*
    Coagulase negative Staphylococci (CoNS), for instance *Staphylococcus epidermidis, Staphylococcus haemolyticus, Staphylococcus lugdunensis, Staphylococcus simulans, Staphylococcus hominis*, wherein the CoNS is preferably *Staphylococcus epidermidis*,
    Methicillin-susceptible or methicillin-resistant Staphylococci wherein the *Staphylococcus* is preferably *Staphylococcus aureus* or *Staphylococcus epidermidis*,
    *Staphylococcus aureus* strains, or CONS strains wherein said strains are resistant to one or more antibiotic and wherein said antibiotic is preferably selected from β-lactams, Cephalosporins, Glycopeptides such as Vancomycin, Linezolid, Lincosamides such as Clindamycin, Rifampicin, Lipopeptides such as Daptomycin, Fluoroquinolones, Trimethoprim/Sulfamethoxazole, Fosfomycin, Fusidic acid, Tigecycline, Tetracyclines, and Dalbavancin, and wherein the CoNS strains is preferably *Staphylococcus epidermidis*,
    Multidrug resistant *Staphylococcus* strains wherein the multidrug resistant *staphylococcus* strain is preferably selected from the group consisting of Multidrug resistant *Staphylococcus aureus* strains and Multidrug resistant CoNS strains, and wherein the Multidrug resistant CoNS strains is preferably *Staphylococcus epidermidis*,
    wherein, preferably the *staphylococcus* bacterium is *Staphylococcus aureus* and/or CoNS wherein the CoNs is preferably *S. epidermidis*.

4. Afabicin for use according to any one of items 1 to 3, wherein the bacterial infection is associated with an open wound and/or wet wound and/or a wound with drainage in place, and preferably wherein the bacterial infection is associated with an open wound.

5. Afabicin for use according to any one of items 1 to 4, wherein the Afacicin in combination with the at least one further agent is administered during a perioperative period and is preferably administered pre and/or post operatively.

6. Afabicin for use according to any one of items 1 to 5, wherein the bacterial infection involves biofilm that contains *staphylococcus* bacteria resistant to rifampicin.

7. Afabicin for use according to any one of items 1 to 6, wherein the bacterial infection involves biofilm that contains methicillin-resistant staphylococci, and preferably wherein the staphylococci is *Staphylococcus aureus* or a CoNS wherein the CoNS is preferably *Staphylococcus epidermidis*.

8. Afabicin for use according to any one of items 1 to 7, wherein the bacterial infection is selected from the group consisting of:
    a medical implant associated infection,
    osteomyelitis,
    infections in cystic fibrosis patients,
    pleuropulmonary infections such as *pneumoniae*, preferably wherein the pleuropulmonary infection is chronic, and more preferably wherein the
pleuropulmonary infections is obstructive pulmonary disease,
endocarditis and preferably wherein the endocarditis is native valve endocarditis,
wound infections, preferably wherein said wound infections are chronic,
mastitis,
sinusitis, preferably wherein said sinusitis is chronic,
otitis media, preferably wherein said otitis media is chronic,
urinary tract infections,
tonsillitis, preferably wherein said tonsillitis is chronic,
laryngitis, preferably wherein said laryngitis is chronic,
infection associated with kidney stones
biliary tract infections,
aerobic vaginitis,
septic thrombophlebitis,
infections associated with intracellular biofilms, for instance in Kupffer cells or in tonsillar cells, and
colonization by *Staphylococcus aureus* that predisposes the patient to infections.
9. Afabicin for use according to any one of items 1 to 8, wherein the bacterial infection is a medical implant associated infection and wherein the medical implant is a permanent indwelling device and preferably is a prosthetic joint.
10. Afabicin for use according to any one of items 1 to 9, wherein the bacterial infection is a medical implant associated infection and preferably is selected from a catheter-associated infection, an infection associated with endotracheal tubes, an infection associated with voice prostheses, an infection associated with soft tissue fillers wherein said soft tissue fillers can be permanent or semi-permanent.
11. Afabicin for use according to any one of items 1 to 10, wherein the method includes a step of debridement in addition to the administration of Afabicin in combination with the at least one further agent.
12. Afabicin for use according to items 8, 9, 10 or 11, wherein said method includes a step of exchanging the medical implant in addition to the administration of Afabicin in combination with the at least one further agent.
13. Afabicin for use according to item 12, wherein the step of administering Afabicin in combination with the at least one further agent is carried out prior to and/or after the step of exchanging the medical implant, and wherein said administration is preferably carried out prior to and after the step of exchanging the medical implant.
14. Afabicin for use according to any one of items 1 to 13, wherein Afabicin is administered intravenously, orally, parenterally and/or topically and/or transdermally.
15. Afabicin for use according to any one of items 1 to 14, wherein Afabicin is administered in a first stage intravenously and in a second stage orally.
16. Afabicin for use according to any one of items 1 to 15, wherein the at least one further agent is administered orally, parenterally, transdermally, intravenously and/or topically.
17. Afabicin for use according to items 12 or 13, wherein the method includes a first step of removal of the medical implant, a second step of intravenous administration of Afabicin in combination with the at least one further agent, a third step of introducing a new medical implant, a fourth step of intravenous administration of Afabicin in combination with the at least one further agent and a fifth step of oral administration of Afabicin in combination with the at least one further agent.
18. Afabicin for use according to any one of items 1 to 17, wherein the at least one further agent is selected from the group consisting of Daptomycin, Vancomycin, Surfactin, A54145, Amphomycin, Friulimicin, laspartomycin, WAP-8294A2, Katanosin, Plusbacin A3, Oritavancin, Telavancin, Teicoplanin, Dalbavancin, Ramoplanin, Mannopeptimycin, Clindamycin, Lincomycin and Pirlimycin.
19. Afabicin for use according to item 18, wherein the at least one further agent is Daptomycin and/or Vancomycin and/or Clindamycin.
20. Daptomycin for use in a method of treating bacterial infections involving biofilm that preferably contains *staphylococcus* bacteria, wherein the method is as specified in any of items 1 to 19.
21. Vancomycin for use in a method of treating bacterial infections involving biofilm that preferably contains *staphylococcus* bacteria, wherein the method is as specified in any of items 1 to 19.
22. Clindamycin for use in a method of treating bacterial infections involving biofilm that preferably contains *staphylococcus* bacteria, wherein the method is as specified in any of items 1 to 19
23. Method of treating, in a patient in need thereof, bacterial infections involving biofilm that preferably contains *staphylococcus* bacteria, wherein the method is as specified in any one of items 1 to 19.
24. Pharmaceutical composition for use in a method of treating bacterial infections involving biofilm that preferably contains *staphylococcus* bacteria, the pharmaceutical composition comprising Afabicin and at least one further agent selected from the group consisting of lipopeptides, glycopeptides and lincosamides, preferably at least one further agent selected from group consisting of Daptomycin, Vancomycin, Surfactin, A54145, Amphomycin, Friulimicin, laspartomycin, WAP-8294A2, Katanosin, Plusbacin A3, Oritavancin, Telavancin, Teicoplanin, Dalbavancin, Ramoplanin, Mannopeptimycin, Clindamycin, Lincomycin and Pirlimycin, more preferably Daptomycin and/or Vancomycin and/or Clindamycin, and wherein the method is as specified in any of items 1 to 19.
25. Kit for use in a method of treating bacterial infections involving biofilm that preferably contains *staphylococcus* bacteria, wherein the kit contains Afabicin and at least one further agent selected from the group consisting of lipopeptides, glycopeptides and lincosamides, preferably at least one further agent selected from group consisting of Daptomycin, Vancomycin, Surfactin, A54145, Amphomycin, Friulimicin, laspartomycin, WAP-8294A2, Katanosin, Plusbacin A3, Oritavancin, Telavancin, Teicoplanin, Dalbavancin, Ramoplanin, Mannopeptimycin, Clindamycin, Lincomycin and Pirlimycin, more preferably Daptomycin and/or Vancomycin and/or Clindamycin, and wherein the method is as specified in any of items 1 to 19.

In another more specific aspect, the invention relates to the following:
1. Afabicin for use in a method of treating bacterial infections involving biofilm that contains *staphylococcus* bacteria, wherein the method comprises administering Afabicin in combination with Daptomycin and/or Vancomycin to the patient.

2. Afabicin for use according to item 1, wherein the *staphylococcus* bacteria are selected from the group consisting of:
   *Staphylococcus aureus*, including community-acquired *Staphylococcus aureus*, and hospital-acquired *Staphylococcus aureus*
   Coagulase negative Staphylococci (CoNS), for instance *Staphylococcus epidermidis, Staphylococcus haemolyticus, Staphylococcus lugdunensis, Staphylococcus simulans, Staphylococcus hominis*, wherein the CoNS is preferably *Staphylococcus epidermidis*,
   Methicillin-susceptible or methicillin-resistant Staphylococci wherein the *Staphylococcus* is preferably *Staphylococcus aureus* or *Staphylococcus epidermidis*,
   *Staphylococcus aureus* strains, or CONS strains wherein said strains are resistant to one or more antibiotic and wherein said antibiotic is preferably selected from β-lactams, Cephalosporins, Vancomycin, Linezolid, Clindamycin, Rifampicin, Daptomycin, Fluoroquinolones, Trimethoprim/Sulfamethoxazole, Fosfomycin, Fusidic acid, Tigecycline, Tetracyclines, and Dalbavancin, and wherein the CoNS strains is preferably *Staphylococcus epidermidis*,
   Multidrug resistant *Staphylococcus* strains wherein the multidrug resistant *staphylococcus* strain is preferably selected from the group consisting of Multidrug resistant *Staphylococcus aureus* strains and Multidrug resistant CONS strains, and wherein the Multidrug resistant CONS strains is preferably *Staphylococcus epidermidis*,
   wherein, preferably the *staphylococcus* bacterium is *Staphylococcus aureus* and/or CONS wherein the CoNs is preferably *S. epidermidis*.

3. Afabicin for use according to item 1, or 2, wherein the bacterial infection is associated with an open wound and/or wet wound and/or a wound with drainage in place, and preferably wherein the bacterial infection is associated with an open wound.

4. Afabicin for use according to item 1, 2 or 3, wherein the Afacicin in combination with Daptomycin and/or Vancomycin is administered during a perioperative period and is preferably administered pre and/or post operatively.

5. Afabicin for use according to item 1, 2, 3 or 4, wherein the bacterial infection involves biofilm that contains *staphylococcus* bacteria resistant to rifampicin.

6. Afabicin for use according to any one of item 1 to 5, wherein the bacterial infection involves biofilm that contains methicillin-resistant staphylococci, and preferably wherein the staphylococci is *Staphylococcus aureus* or a CoNS wherein the CoNS is preferably *Staphylococcus epidermidis*.

7. Afabicin for use according to any one of items 1 to 6, wherein the bacterial infection is selected from the group consisting of:
   a medical implant associated infection,
   osteomyelitis,
   infections in cystic fibrosis patients,
   pleuropulmonary infections such as *pneumoniae*, preferably wherein the pleuropulmonary infection is chronic, and more preferably wherein the pleuropulmonary infections is obstructive pulmonary disease,
   endocarditis and preferably wherein the endocarditis is native valve endocarditis,
   wound infections, preferably wherein said wound infections are chronic,
   mastitis,
   sinusitis, preferably wherein said sinusitis is chronic,
   otitis media, preferably wherein said otitis media is chronic,
   urinary tract infections,
   tonsillitis, preferably wherein said tonsillitis is chronic,
   laryngitis, preferably wherein said laryngitis is chronic,
   infection associated with kidney stones
   biliary tract infections,
   aerobic vaginitis,
   septic thrombophlebitis,
   infections associated with intracellular biofilms, for instance in Kupffer cells or in
   tonsillar cells, and
   colonization by *Staphylococcus aureus* that predisposes the patient to infections.

8. Afabicin for use according to any one of items 1 to 7, wherein the bacterial infection is a medical implant associated infection and wherein the medical implant is a permanent indwelling device and preferably is a prosthetic joint.

9. Afabicin for use according to any one of items 1 to 8, wherein the bacterial infection is a medical implant associated infection and preferably is selected from a catheter-associated infection, an infection associated with endotracheal tubes, an infection associated with voice prostheses, an infection associated with soft tissue fillers wherein said soft tissue fillers can be permanent or semi-permanent.

10. Afabicin for use according to any one of items 1 to 9, wherein the method includes a step of debridement in addition to the administration of Afabicin in combination with Daptomycin and/or Vancomycin.

11. Afabicin for use according to items 7, 8, 9 or 10, wherein said method includes a step of exchanging the medical implant in addition to the administration of Afabicin in combination with Daptomycin and/or Vancomycin.

12. Afabicin for use according to item 11, wherein the step of administering Afabicin in combination with Daptomycin and/or Vancomycin is carried out prior to and/or after the step of exchanging the medical implant, and wherein said administration is preferably carried out prior to and after the step of exchanging the medical implant.

13. Afabicin for use according to any one of items 1 to 12, wherein Afabicin is administered intravenously, orally, parenterally and/or topically and/or transdermally.

14. Afabicin for use according to any one of items 1 to 13, wherein Afabicin is administered in a first stage intravenously and in a second stage orally.

15. Afabicin for use according to any one of items 1 to 14, wherein Daptomycin and/or Vancomycin is administered intravenously and/or topically.

16. Afabicin for use according to item 11 or 12, wherein the method includes a first step of removal of the medical implant, a second step of intravenous administration of Afabicin in combination with Daptomycin and/or Vancomycin, a third step of introducing a new medical implant, a fourth step of intravenous administration of Afabicin in combination with Daptomycin and/or Vancomycin and a fifth step of oral administration of Afabicin in combination with Daptomycin and/or Vancomycin.

17. Daptomycin for use in a method of treating bacterial infections involving biofilm that contains *staphylococcus* bacteria, wherein the method is as specified in any of items 1 to 16.
18. Vancomycin for use in a method of treating bacterial infections involving biofilm that contains *staphylococcus* bacteria, wherein the method is as specified in any of items 1 to 16.
19. Method of treating, in a patient in need thereof, bacterial infections involving biofilm that contains *staphylococcus* bacteria, wherein the method is as specified in any one of items 1 to 16.

Further embodiments of the present invention become apparent from the detailed description of the invention provided below.

5. DESCRIPTION OF FIGURES

Figure 3:
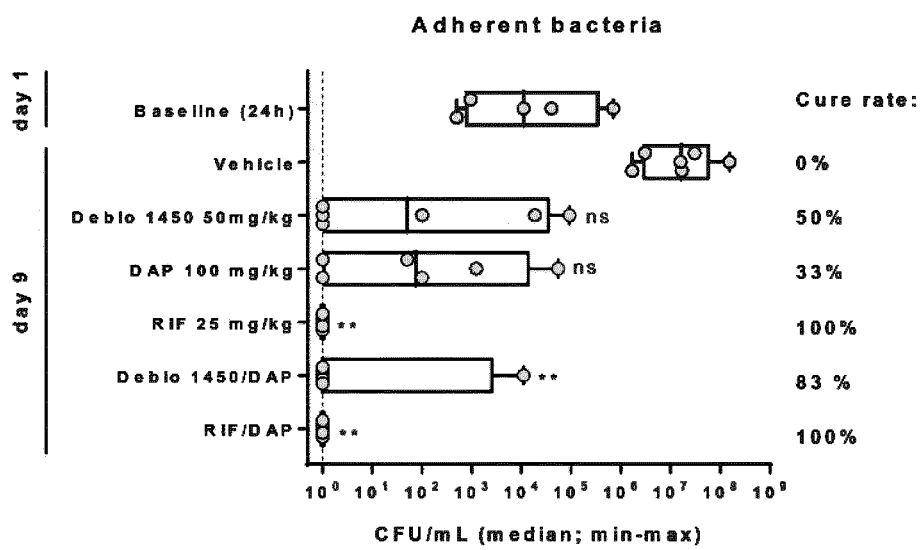

FIG. 3 shows the Effect of a 5.5-day antibiotic treatment on biofilm-embedded bacteria in a mouse tissue cage model. The adherent bacterial fraction was determined by plating of medium after sonication of explanted tissue cages from infected untreated control animals at 24h post-infection (baseline, before treatment) and from antibiotic- and vehicle-treated animals on day 9. Cure rate is indicated. Statistical analysis of comparison between the vehicle vs. treatment groups was performed with nonparametric Kruskal-Wallis test, followed by Dunn's multiple comparisons test (**$p<0.005$); ns=not significant.

Figure 4:
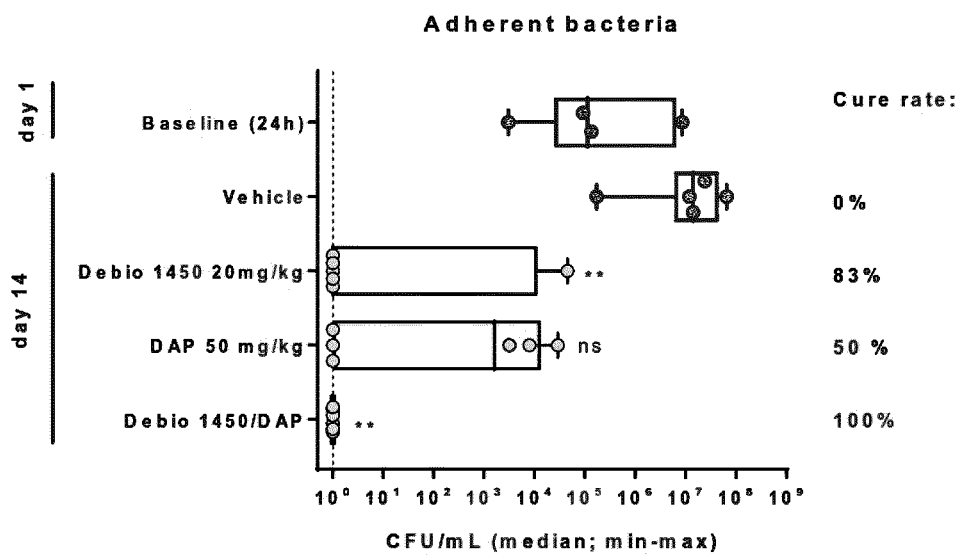

FIG. 4 depicts the Effect of an 11-day antibiotic treatment on biofilm-embedded bacteria in a mouse tissue cage model. The adherent bacterial fraction was determined by plating of medium after sonication of explanted tissue cages from infected untreated control animals at 24h post-infection (baseline, before treatment) and from antibiotic- and vehicle-treated animals on day 14. Cure rate is indicated. Statistical analysis of comparison between the vehicle vs. treatment groups was performed with nonparametric Kruskal-Wallis test, followed by Dunn's multiple comparisons test (**$p<0.005$); ns=not significant.

6. DETAILED DESCRIPTION OF THE INVENTION

6.1. Definitions

The following definitions are provided to assist the reader. Unless otherwise defined, all terms of art, notations, and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not be construed as representing a substantial difference over the definition of the term as generally understood in the art. In case of ambiguity, the definitions and information contained in WO 2013/190384 A shall be used on an auxiliary basis and to the extent that they are consistent with the present invention. As a supplementary source of information, chemical, pharmaceutical and medical dictionaries and especially Römpp "Lexikon Chemie", Thieme Verlag 1999; Remington "The Science and Practice of Pharmacy", Pharmaceutical Press, 2012; and "Stedman's Medical Dictionary", Wolters Kluwer, 2006 are to be used as further supplementary sources of information, but only to the extent that they are consistent with the information provided herein and in WO 2013/190384 A. Unless specified otherwise, references to internet pages are to be understood as references to the respective pages in the version of Jun. 14, 2019.

Unless the context dictates otherwise, the term "a" or "an" characterizes a substance or component but without restricting its number/amount. For instance, a reference to "a binder" is to be understood as a reference to a single binder or, alternatively, a combination of two or more binders. The same applies if no article is used. For instance, an "infection associated with biofilm" may be associated with one, two or more separate biofilm colonies.

In some embodiments, the term "about" refers to a deviation of +10% from the recited value. When the word "about" is used herein in reference to a number, it should be understood that still another embodiment of the invention includes that number not modified by the presence of the word "about".

"Administering" or "administration of" a drug to a patient (and grammatical equivalents of this phrase) refers to direct administration, which may be administration to a patient by a medical professional or may be self-administration, and/or indirect administration, which may be the act of prescribing a drug. E.g., a physician who instructs a patient to self-administer a drug or provides a patient with a prescription for a drug is administering the drug to the patient.

In the context of the present invention, the term "biofilm" is used to refer to structured aggregations of microbial cells of one or more species encased in a self-produced matrix and adherent to a biotic or abiotic surface. In the context of the present invention, the term "biofilm" is used to refer also to structured aggregations of microbial cells, as defined above, but which have been detached from the biotic or abiotic surface by debridement and/or other physical and/or surgical methods.

The term "combination product" can refer to (i') a product comprised of two or more regulated components that are physically, chemically, or otherwise combined or mixed and produced as a single entity; (ii') two or more separate products packaged together in a single package or as a unit and comprised of drug and device products, device and biological products, or biological and drug products; (iii') a drug, device, or biological product packaged separately that according to its investigational plan or proposed labeling is intended for use only with an approved individually specified drug, device, or biological product where both are required to achieve the intended use, indication, or effect and where upon approval of the proposed product the labeling of the approved product would need to be changed, e.g., to reflect a change in intended use, dosage form, strength, route of administration, or significant change in dose; or (iv') any investigational drug, device, or biological product packaged separately that according to its proposed labeling is for use only with another individually specified investigational drug, device, or biological product where both are required to achieve the intended use, indication, or effect.

"Combination therapy", "in combination with" or "in conjunction with" as used herein denotes any form of concurrent, parallel, simultaneous, sequential or intermittent treatment with at least two distinct treatment modalities (i.e., compounds, components, targeted agents or therapeutic agents). As such, the terms refer to administration of one treatment modality before, during, or after administration of the other treatment modality to the subject. The modalities in combination can be administered in any order. The therapeutically active modalities are administered together (e.g., simultaneously in the same or separate compositions, formulations or unit dosage forms) or separately (e.g., on the same day or on different days and in any order as according to an appropriate dosing protocol for the separate compositions, formulations or unit dosage forms) in a manner and dosing regimen prescribed by a medical care taker or according to a regulatory agency. In general, each treatment modality will be administered at a dose and/or on a time schedule determined for that treatment modality. Optionally, three or more modalities may be used in a combination therapy. Additionally, the combination therapies provided herein may be used in conjunction with other types of treatment. For example, other antibiotic agents may additionally be administered.

The verbs "comprise" and "contain" introduce an open list that allows the additional presence of further components not included in said list. By contrast, the verb "consist of" introduces a closed list that does not permit the additional presence of further unmentioned components. Wherever the present application uses the verbs "comprise" or "contain", this is meant to include the option "consist of" as a preferred embodiment.

The present application refers to "components" of the pharmaceutical compositions of the present invention as any material that is present in the final product, including excipients and including also the pharmaceutically active ingredient. The term "components" also includes a tablet coating (if present) or a capsule shell (if present). "Excipients" are all components of the pharmaceutical composition that do not exercise a pharmaceutical effect on their own, i.e. all components other than the pharmaceutically active ingredient.

An infection is "difficult to treat" if it involves biofilm formed by difficult-to-treat microorganisms. These are in particular microorganisms resistant to antibiotics, especially resistant to antibiotics for oral administration, such as Rifampicin-resistant staphylococci, enterococci, and quinolone-resistant gram-negative bacilli and fungi.

"Dose" and "dosage" refer to a specific amount of active or therapeutic agents for administration. Such amounts are included in a "dosage form," which refers to physically discrete units suitable as unitary dosages for human subjects and other mammals, each unit containing a predetermined quantity of active agent calculated to produce the desired onset, tolerability, and therapeutic effects, in association with one or more suitable pharmaceutical excipients such as carriers.

The terms "individual", "patient" or "subject" are used interchangeably in the present application and are not meant to be limiting in any way. The "individual", "patient" or "subject" can be of any age, sex and physical condition. Preferably, the methods of treatment and combination products of the present invention are for use in a human patient. In other words, the individual, patent or subject is preferably human. All references to an "individual", "patient" or "subject" herein are also to be understood as references to a human "human individual", "human patient" or "human subject".

"Infections involving biofilm", "biofilm-associated infections" and the like terms are used herein to characterize bacterial infections wherein the bacteria have formed a biofilm. It is not always clear whether a biofilm has indeed formed, e.g. because this fact cannot be established due to the condition of the patient. In such a situation, it is possible to employ the combination therapy of the present invention. This may be regarded as a prophylactic treatment to prevent the formation of a biofilm. Likewise, any reference herein to an infection that may exist with or without biofilm is intended as a reference to the respective infection, wherein biofilm has formed or may have formed.

"Infusion" or "infusing" refers to the introduction of a drug-containing solution into the body through a vein for therapeutic purposes. Generally, this is achieved via an intravenous bag.

"Pharmaceutically acceptable" is used in the context of the present invention to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable carrier" or "pharmaceutically acceptable diluent" means any and all solvents, dispersion media, coatings, antibacterial and antifungal agents, isotonic and absorption delaying agents, compatible with pharmaceutical administration. The use of such media and agents for pharmaceutically active substances is well known in the art. Acceptable carriers, excipients, or stabilizers are nontoxic to recipients at the dosages and concentrations employed and, without limiting the scope of the present invention, include: additional buffering agents; preservatives; co-solvents; antioxidants, including ascorbic acid and methionine; chelating agents such as EDTA; metal complexes (e.g., Zn-protein complexes); biodegradable polymers, such as polyesters; salt-forming counterions, such as sodium, polyhydric sugar alcohols; amino acids, such as alanine, glycine, glutamine, asparagine, histidine, arginine, lysine, ornithine, leucine, 2-phenylalanine, glutamic acid, and threonine; organic sugars or sugar alcohols, such as lactitol, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, [alpha]-monothioglycerol, and sodium thio sulfate; low molecular weight proteins, such as human serum albumin, bovine serum albumin, gelatin, or other immunoglobulins; and hydrophilic polymers, such as polyvinylpyrrolidone. Other pharmaceutically acceptable carriers, excipients, or stabilizers, such as those described in Remington's Pharmaceutical Sciences 16th edition, Osol, A. Ed. (1980) may also be included in a pharmaceutical composition described herein, provided that they do not adversely affect the desired characteristics of the pharmaceutical composition.

"Pharmaceutically acceptable salt" is used in the context of the present invention to characterize any form of ionic species (acid addition salt, base addition salt, zwitterionic/internal salt, etc.) of the drug, which is pharmaceutically acceptable as defined above. Unless specified otherwise, all references to pharmaceutically active compounds in the present application should be understood as references to the respective compounds in the free form and also as references to pharmaceutically acceptable salts of the respective compounds.

The term "therapeutically effective amount" refers to an amount of drug substance, e.g. Afabicin and/or the at least one further agent selected from the group consisting of lipopeptides, glycopeptides and lincosamides, which has a therapeutic effect and which, in particular, is able to treat biofilm-associated *staphylococcus* infections. The therapeutically effective amount of the drug can reduce the number of bacterial cells; reduce the biofilm size or burden; inhibit (i.e., slow to some extent and in a certain embodiment, stop) bacterial cell infiltration into peripheral organs; inhibit (i.e., slow to some extent and in a certain embodiment, stop) biofilm growth; relieve to some extent one or more of the symptoms associated with the infection; or any combination thereof. A "prophylactically effective amount" refers to an amount effective, at dosages and for periods of time necessary, to achieve the desired prophylactic result in a patient at risk of biofilm-associated *staphylococcus* infection. Typically but not necessarily, since a prophylactic dose is used in subjects prior to or at an earlier stage of disease, the prophylactically effective amount will be less than the therapeutically effective amount. Nonetheless, a therapeutically effective amount is also a prophylactically effective amount.

The terms "treatment" and "therapy", as used in the present application, refer to a set of hygienic, pharmacological, surgical and/or physical means used with the intent to cure and/or alleviate a disease and/or symptoms with the goal of remediating the health problem. The terms "treatment" and "therapy" include preventive and curative methods, since both are directed to the maintenance and/or reestablishment of the health of an individual or animal. Regardless of the origin of the symptoms, disease and disability, the administration of a suitable medicament to alleviate and/or cure a health problem should be interpreted as a form of treatment or therapy within the context of this application.

"Unit dosage form" as used herein refers to a physically discrete unit of therapeutic formulation appropriate for the subject to be treated. It will be understood, however, that the total daily usage of the compositions of the present invention will be decided by the attending physician within the scope of sound medical judgment. The specific effective dose level for any particular subject or organism will depend upon a variety of factors including the disorder being treated and the severity of the disorder; activity of specific active agent employed; specific composition employed; age, body weight, general health, sex and diet of the subject; time of administration, and rate of excretion of the specific active agent employed; duration of the treatment; drugs and/or additional therapies used in combination or coincidental with specific compound(s) employed, and like factors well known in the medical arts.

The term "medical implant" as used herein refers to any indwelling (placed inside the body of a patient) medical device intended to replace, support or enhance a biological structure. Medical implants may be placed permanently, e.g. a stent or prosthetic joint, alternatively they can be placed on a temporary basis and removed when they are no longer needed e.g. a chemotherapy port or orthopedic screw.

Non-limiting examples of medical implants include stents, shunts e.g. ventricular shunts, ventricular assisted devices, vascular grafts, vascular clips, artificial joints, cardioverter defibrillators (defibrillators), pacemakers, prosthetic joint e.g. artificial hips and knee joints, artificial heart valves, breast implants, orthopedic screws, orthopedic rods, orthopedic plates, artificial spinal discs, intra-uterine devices (IUDs), coronary stents, ear tubes, intra-ocular lenses, contact lenses, catheters e.g. central venous catheters, peripheral vascular catheters, peritoneal dialysis catheters, urinary catheters, endotracheal tubes, voice prostheses, soft tissue fillers (permanent or semi-permanent tissue fillers).

The term "antibiotic implant" as used herein refers to any indwelling (placed inside the body of a patient) medical device, wherein said medical device is implanted in a patient with the primary intention of treating or preventing infection e.g. bacterial infection through the delivery of antibiotics. Antibiotic implants may be placed permanently, alternatively they can be placed on a temporary basis and removed when they are no longer needed e.g. when an infection has been eradicated, or they may simply dissolve over time in the body.

Non limiting examples of antibiotic implants include antibiotic loaded beads or spacers.

The present invention relates to combinations of Afabicin with at least one further agent selected from the group consisting of lipopeptides, glycopeptides and lincosamides for use in combination therapies, combination products, pharmaceutical compositions containing drug combinations, kits containing such drug combinations in separate containers, pharmaceutical compositions containing one of these drugs for use in combination with the respective other drug (and vice versa) as well as methods of treatment comprising the administration of at least one of these products. Unless the context dictates otherwise, all references to any one of the above-mentioned aspects of the present invention should also be understood as references to the other aspects of the present invention as listed above. For instance, references to the method of the present invention should also be understood as disclosures of pharmaceutical compositions of the present invention that are to be used in these methods. Likewise, references to the pharmaceutical compositions of the present invention should also be understood as disclosures of methods of the present invention using these pharmaceutical compositions.

Unless specified otherwise, all absolute amount indications in the present application are given in mg. Unless specified otherwise, all relative amount indications are provided in weight % (wt %) based on the total weight of the pharmaceutical composition. If the pharmaceutical composition is in the form of a coated tablet, the weight of the coating is not included in said total weight. If the pharmaceutical composition is in the form of a capsule, the weight of the capsule shell is also excluded from said total weight. The weight of any liquid that may be temporarily present during wet granulation, but which is removed by subsequent drying procedures, is not included in said total weight.

Unless specified otherwise, all absolute amount indications, e.g., daily dosages, of the active substance Afabicin are based on the molecular weight of the free acid form. Hence, if a salt form of Afabicin is used, the specified absolute amounts need to be converted taking relative molecular weights into account. This can be done using the following equation (1):

$$m(\text{salt}) = m(\text{free acid}) * M(\text{salt})/M(\text{free acid}) \qquad (1)$$

wherein m specifies the absolute amount and M specifies the molecular weight of the respective form.

Unless specified otherwise, all relative amount indications, e.g. compositional ranges, of the active substance Afabicin are based on the molecular weight of the bis-ethanolamine salt of Afabicin (Afabicin Olamine). Hence, if a different salt form or the free acid form of Afabicin is used, the specified absolute amounts need to be converted taking relative molecular weights into account. This can be done using the following equation (2):

$$w(s2)=100*w(s1)*M(s2)/(M(s1)*(100+w(s1)*(M(s2)-M(s1))/M(s1))) \quad (2)$$

wherein w(s2) is the relative amount of a second salt form or the free acid form (in wt % based on the total weight of the composition containing this salt form); w(s1) is the relative amount of the bis-ethanolamine salt form (in wt % based on the total weight of the composition containing the bis-ethanolamine salt form; M(s2) is the molecular weight of said second salt form or the free acid form; and M(s1) is the molecular weight of the bis-ethanolamine salt form.

Indications in the present application that the pharmaceutical compositions of the present invention are "free" of a particular substance, indications that no substance of this type is present, as well as statements that said substance is absent, omitted, or the like, are to be understood such that the relative amount of said substance in the pharmaceutical composition is less than 0.1 wt % and preferably less than 0.01 wt %. According to a particularly preferred embodiment, said substance is completely absent or present only in such a small amount that it cannot be detected based on analytical techniques available at the filing date. According to another embodiment, the pharmaceutical composition contains the respective substance in such a small amount that it has no measurable impact on the dissolution characteristics of the active ingredient Afabicin.

Although the present invention is described hereinbelow primarily by describing "specific embodiments" of the invention (or using similar terminology such as "certain embodiments", etc.), such disclosures of multiple embodiments should also be understood as disclosures of the respective combinations of features, unless the context dictates otherwise

6.2. Overview

Infections associated with biofilms are very difficult to treat and there are many cases in which antibiotic drugs that are therapeutically active against a particular bacterium in the planktonic state are not therapeutically active against the same bacterium when being present in the form of biofilm. For this reason there are only a few effective treatments for infections associated with biofilms.

Afabicin is known to be effective in the treatment of planktonic state *staphylococcus* infections, but it was unknown whether Afabicin is also effective in the treatment of biofilm-associated infections involving *staphylococcus* bacteria. Preliminary experiments revealed that Afabicin shows only moderate anti-biofilm activity when used as a monotherapy. The same is true for many other antibiotic drugs, including Daptomycin and/or Vancomycin.

The present invention is based on the surprising finding that an effective treatment of biofilm infections, more specifically biofilm infections involving *staphylococcus* bacteria, can be provided when combining Afabicin with at least one further antibiotic agent selected from the group consisting of lipopeptides, glycopeptides and lincosamides. Preferably said at least one further agent is selected from the group consisting of Daptomycin, Vancomycin, Surfactin, A54145, Amphomycin, Friulimicin, Iaspartomycin, WAP-8294A2, Katanosin, Plusbacin A3, Oritavancin, Telavancin, Teicoplanin, Dalbavancin, Ramoplanin, Mannopeptimycin, Clindamycin, Lincomycin and Pirlimycin, more preferably it is Daptomycin and/or Vancomycin and/or Clindamycin. In all embodiments of the present invention, these agents may either be used in the free form or in the form of a pharmaceutically acceptable salt. Similarly, there is also no particular restriction regarding the possible use of hydrates, solvates and/or polymorphs of any of these agents. References to the Afabicin and/or any of the above further agents are thus to be understood as encompassing also references to the respective pharmaceutically acceptable salts, hydrates, solvates and polymorphs. The present invention thus provides treatments of biofilm infections and preferably biofilm infections involving *staphylococcus* bacteria that involve the use of a combination of Afabicin with at least one further antibiotic agent selected from the group consisting of lipopeptides, glycopeptides and lincosamides, such as preferably the agents listed above and more preferably Daptomycin and/or Vancomycin and/or Clindamycin. This includes a provision of Afabicin for use in combination with at least one further antibiotic agent selected from the group consisting of lipopeptides, glycopeptides and lincosamides in the treatment of biofilm infections and preferably biofilm infections involving *staphylococcus* bacteria; it also includes a provision of Daptomycin and/or vancomycin and/or Clindamycin for use in combination with Afabicin in the treatment of biofilm infections and preferably biofilm infections involving *staphylococcus* bacteria; it further includes the provision of a combination of Afabicin with at least one further antibiotic agent selected from the group consisting of lipopeptides, glycopeptides and lincosamides, such as preferably the agents listed above and more preferably Daptomycin and/or Vancomycin and/or Clindamycin for the treatment of biofilm-infections and preferably biofilm infections involving *staphylococcus* bacteria. It also includes methods of treating biofilm infections and preferably biofilm infections involving *staphylococcus* bacteria in patients in need thereof, including the administration of Afabicin in combination with the administration of at least one further antibiotic agent selected from the group consisting of lipopeptides, glycopeptides and lincosamides, such as preferably the agents listed above and more preferably Daptomycin and/or Vancomycin and/or Clindamycin.

Afabicin and the at least one further agent may or may not be present in the same composition. The two or more drugs may be administered in the form of different pharmaceutical compositions, by different administration routes, at different administration times and at different administration intervals, etc.

6.3. Afabicin

Afabicin is the INN name for {6-[(1E)-3-{methyl [(3-methyl-1-benzofuran-2-yl)methyl]amino}-3-oxoprop-1-en-1-yl]-2-oxo-3,4-dihydro-1,8-naphthyridin-1 (2H)-yl} methyl dihydrogen phosphate. Other names of this compound are ((E)-6-[(N-methyl-((3-methylbenzofuran-2-yl)methyl)amino)-3-oxoprop-1-en-1-yl)-2-oxo-3,4-dihydro-1, 8-naphthyridin-1 (2H)-yl]methyl phosphate and (2E)-2-Propenamide, N-methyl-N-[(3-methyl-2-benzofuranyl) methyl]-3-[5,6,7,8-tetrahydro-7-oxo-8-[(phosphonooxy) methyl]-1,8-naphthyridin-3-yl]. It is sometimes also referred to Debio 1450. It is a *staphylococcus*-selective antibiotic drug, which is active as a FabI inhibitor. It is noteworthy that Afabicin is active also against staphylococci strains that are resistant to the antibiotics including β-Lactams, Vancomycin, Daptomycin and Linezolid. Afabicin is also active against methicillin-resistant *Staphylococcus aureus* (MRSA). Afabicin has the following structure:

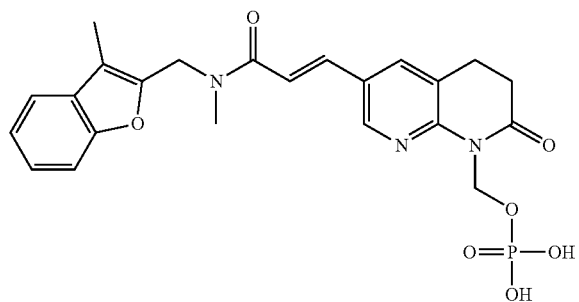 [SMILES: Cc1c(CN(C)C(=O)/C=C/c2cnc3c(c2)CCC(=O)N3COP(=O)(O)O)oc2ccccc12]

The free acid form of Afabicin has been attributed the following CAS RN 1518800-35-5.

Afabicin (Debio 1450) is described inter alia in WO 2013/190 384. The specific use of Afabicin in the treatment of diabetic foot infections is described in WO 2017/144 717. The disclosures of these earlier applications are incorporated by reference in their entirety into the present application.

All references to Afabicin in the present application should be understood as references to Afabicin in the free acid form as shown above or, alternatively, as references to pharmaceutically acceptable salts of Afabicin. A preferred embodiment relates to the use of the bis-ethanol ammonium salt or BES of Afabicin (sometimes also referred to as Afabicin Olamine or the bis-ethanolamine salt of Afabicin or Debio 1450 BES). The CAS RN 1518800-36-6 has been attributed to this bis-ethanolamine salt. A mixture of the free acid form and the bis-ethanolamine salt of Afabicin is also advantageously used. According to a particularly preferred embodiment of the present application, all references to Afabicin are to be understood as references to the Afabicin bis-ethanolamine salt optionally in combination with Afabicin in the free acid form. In the most preferred embodiment, a combination of Afabicin bis-ethanolamine salt with Afabicin in the free acid form is used, wherein the molar ratio of free acid to bis-ethanolamine salt is in the range of from 0.7 to 0.9 and even more preferably from 0.75 to 0.85.

Afabicin is a prodrug. The pharmaceutically active metabolite is (E)-N-methyl-N-((3-methylbenzofuran-2-yl)methyl)-3-(7-oxo-5,6,7,8-tetrahydro-1,8-naphthyridin-3-yl)acrylamide, also referred to as Debio 1452 (sometimes also referred to as AFN-1252) and its CAS RN is 620175-39-5. It has the following structure:

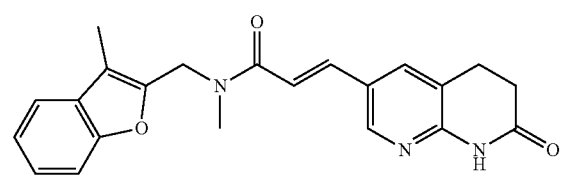 [SMILES: Cc1c(CN(C)C(=O)/C=C/c2cnc3c(c2)CCC(=O)N3)oc2ccccc12]

According to yet another embodiment of the present invention, it is possible to use the parent compound Debio 1452 or pharmaceutically acceptable salts thereof instead of the prodrug compound. According to this embodiment, references to the use of Afabicin should thus be understood as references to Debio 1452 with the proviso that Debio 1452 is more restricted in terms of the feasible administration forms.

6.4. Daptomycin

Daptomycin is a naturally occurring lipo-peptide of the following structure:

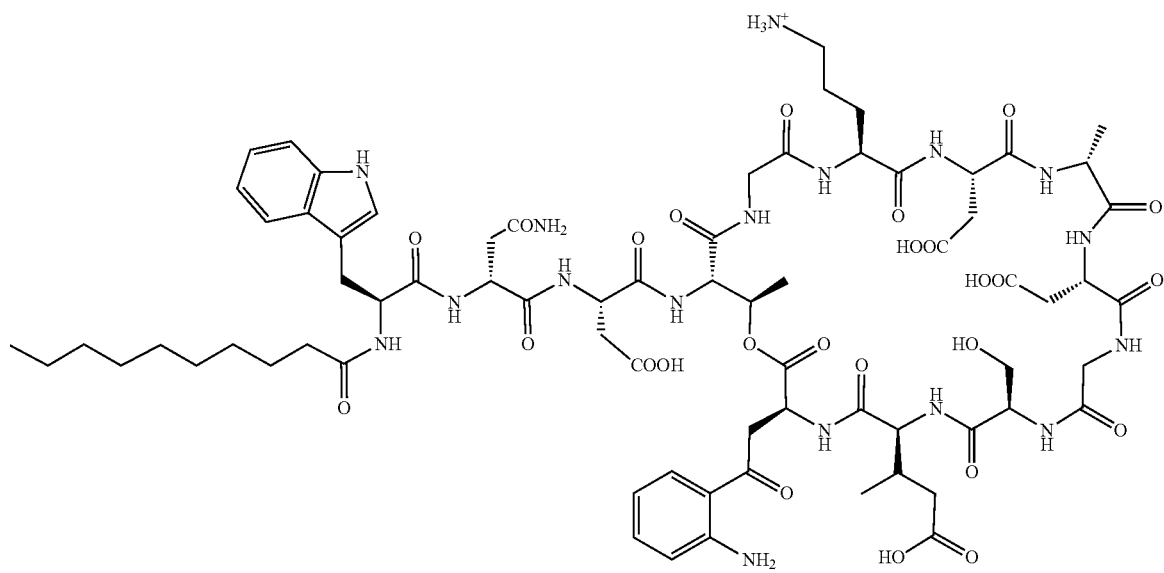 [SMILES: CCCCCCCCCC(=O)N[C@@H](Cc1c[nH]c2ccccc12)C(=O)N[C@H](CC(N)=O)C(=O)N[C@@H](CC(=O)O)C(=O)CN[C@@H]1C(=O)NCC(=O)N[C@@H](CCC[NH3+])C(=O)N[C@@H](CC(=O)O)C(=O)N[C@H](C)C(=O)N[C@@H](CC(=O)O)C(=O)NCC(=O)N[C@H](CO)C(=O)N[C@@H](C(C)CC(=O)O)C(=O)N[C@@H](CC(=O)c2ccccc2N)C(=O)O[C@@H]1C]

Daptomycin is marketed in the EU by Novartis and in the US by Cubist Pharmaceuticals. It has a mode of action wherein it is incorporated into bacterial cell membranes to generate holes in the membranes that result in depolarization and ultimately death of the bacterial cell. It is typically administered by intravenous injection or infusion. It is marketed under the trade name Cubicin®. Details on its practical applications can be found in the summary of product characteristics as published by the European Medicines Agency under: ema.europa.eu/en/documents/product-information/cubicin-epar-product-information_en.pdf.

6.5. Vancomycin

Vancomycin is a glycopeptide antibiotic drug. It has the following structure:

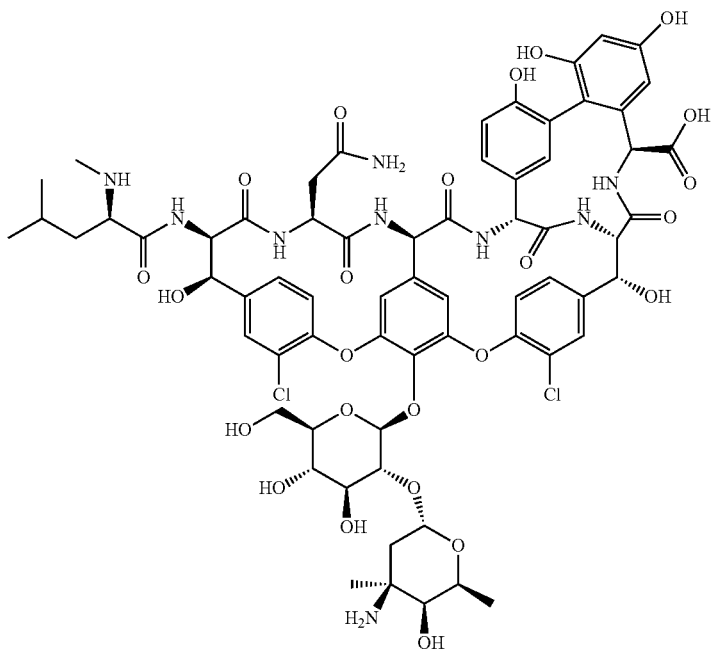 [SMILES: CN[C@H](CC(C)C)C(=O)N[C@H]1C(=O)N[C@@H](CC(N)=O)C(=O)N[C@H]2C(=O)N[C@H]3C(=O)N[C@H](C(=O)N[C@H](C(=O)O)c4cc(O)cc(O)c4-c4cc3ccc4O)[C@H](O)c3ccc(c(Cl)c3)Oc3cc2cc(c3O[C@@H]2O[C@H](CO)[C@@H](O)[C@H](O)[C@H]2O[C@H]2C[C@](C)(N)[C@H](O)[C@H](C)O2)Oc2ccc(cc2Cl)[C@H]1O]

Vancomycin was developed by Eli Lilly. It is inter alia available under the trade name Vancocin®. It works by being incorporated into the cell membrane of gram-positive bacteria, which leads to a weakening and ultimately destruction of the cell membrane due to osmotic pressure. It is typically administered intravenously. Details on its use can be found in the respective Wikipedia entry "Vancomycin" (Version of May 17, 2019), references cited therein and in the published Summary of Product Characteristics, which can be found inter alia under medicines.org.uk/emc/product/6255/smpc#PRODUCTINFO.

6.6. Clindamycin

Clindamycin acts as a bacterial protein synthesis inhibitor by inhibiting ribosomal translocation. It has the following chemical structure:

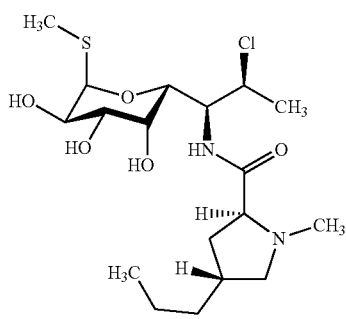

Clindamycin belongs to the group of lincosamide antibiotics. It can be administered orally (in the form of capsules or tablets), topically (as creams or gels) or parenterally (by IV infusion or IM or SC injection). It is commercially available under the tradenames Sobelin® and Cleocin®. Generic versions of the drug are available. Further information on Clindamycin can be found in the respective Wikipedia entry "Clindamycin" (Version of Jun. 5, 2020) and references cited therein. Details on its use can be found in drugs.com/clindamycin.html and also in the published Summary of Product Characteristics, which can be found inter alia under medicines.org.uk/emc/medicine/29227 for the infusion liquid and under medicines.org.uk/emc/product/7337/smpc for the capsules.

6.7. Other Agents

The at least one further agent may also be another agent belonging to the group of lipopeptides, glycopeptides and lincosamides. Members of this group are in particular Surfactin, A54145, Amphomycin, Friulimicin, laspartomycin, WAP-8294A2, Katanosin, Plusbacin A3, Oritavancin, Telavancin, Teicoplanin, Dalbavancin, Ramoplanin, Mannopeptimycin, Lincomycin and Pirlimycin.

Information on lipopeptides can be found, for instance, in R. H. Baltz et al., Nat Prod Rep., 2005 December; 22 (6): 717-41. doi: 10.1039/b416648p. Epub 2005 Nov. 4 (accessible via ncbi.nlm.nih.gov/pubmed/16311632) and literature cited therein.

Information on glycopeptides can be found, for instance, in S. Li and E. S. Starkey Arch Dis Child Educ Pract Ed. 2016 December; 101 (6): 323-326. doi: 10.1136/archdischild-2015-309270. Epub 2016 Jul. 7 (accessible via pubmed.ncbi.nlm.nih.gov/27389546/) and literature cited therein.

Information on lincosamides can be found, for instance, in J. Spízek and T. Rezanka Biochem Pharmacol. 2017 Jun. 1; 133:20-28. doi: 10.1016/j.bcp.2016.12.001. Epub 2016 Dec. 7 (accessible via pubmed.ncbi.nlm.nih.gov/27389546/) and literature cited therein.

Information on Surfactin can be found in the respective Wikipedia entry (as at Jun. 10, 2020) and in R. Sen, Adv Exp Med Biol. 2010; 672:316-23. doi: 10.1007/978-1-4419-5979-9_24 (accessible via pubmed.ncbi.nlm.nih.gov/27940264/) and references cited therein.

Information on A54145 can be found in D. S. Fukuda et al., J Antibiot (Tokyo), 1990 June; 43 (6): 601-6. doi: 10.7164/antibiotics.43.601 (accessible via pubmed.ncbi.nlm.nih.gov/2380108/) and references cited therein.

Information on Amphomycin can be found in M. Singh et al., Scientific Reports| 6:31757| DOI: 10.1038/srep31757 (accessible via nature.com/articles/srep31757.pdf) and literature cited therein.

Information on Friulimicin can be found in the respective Wikipedia entry (as at Jun. 10, 2020) and in T. Schneider et al., Antimicrob Agents Chemother. 2009 April; 53 (4): 1610-8. doi: 10.1128/AAC.01040-08. Epub 2009 Jan. 21 (accessible via pubmed.ncbi.nlm.nih.gov/19164139/) and references cited therein.

Information on Laspartomycin can be found in D. B. Borders et al., Nat. Prod. 2007, 70, 3, 443-446 (accessible via pubs.acs.org/doi/10.1021/np068056f) and references cited therein.

Information on WAP-8294A2 can be found in A. Kato et al. in The Journal of Antibiotics, 64, 373-379, 2011 (accessible via nature.com/articles/ja20119) and references cited therein.

Information on Katanosin can be found in the respective Wikipedia entry (as at Jun. 10, 2020) and in H. Maki et al. Antimicrob Agents Chemother. 2001 June; 45 (6): 1823-7. doi: 10.1128/AAC.45.6.1823-1827.2001 (accessible via pubmed.ncbi.nlm.nih.gov/11353632/) and references cited therein. This latter article also provides information on Plusbacin A3.

Information on Oritavancin can be found in the respective Wikipedia entry (as at Jun. 10, 2020) and in J. Mattox et al. Consult Pharm. 2016 February; 31 (2): 86-95. doi: 10.4140/TCP.n.2016.86. (accessible via pubmed.ncbi.nlm.nih.gov/26842686/) and references cited therein.

Information on Telavancin can be found in the respective Wikipedia entry (as at Jun. 10, 2020) and in B. Das Ther Adv Infect Dis. 2017 March; 4 (2): 49-73. doi: 10.1177/2049936117690501 (accessible via pubmed.ncbi.nlm.nih.gov/28634536/) and references cited therein.

Information on Teicoplanin can be found in the respective Wikipedia entry (as at Jun. 10, 2020) and in K. W. Shea Med Clin North Am. 1995 July; 79 (4): 833-44. doi: 10.1016/s0025-7125 (16) 30042-6 (accessible via pubmed.ncbi.nlm.nih.gov/7791426/) and references cited therein.

Information on Dalbavancin can be found in the respective Wikipedia entry (as at Jun. 10, 2020) and in V. R. Anderson and G. M. Keating Drugs 2008; 68 (5): 639-48; discussion 649-51. doi: 10.2165/00003495-200868050-00006. (accessible via pubmed.ncbi.nlm.nih.gov/18370443/) and references cited therein.

Information on Ramoplanin can be found in the respective Wikipedia entry (as at Jun. 10, 2020) and in D. K. Farver et al. Ann Pharmacother. 2005 May; 39 (5): 863-8. doi: 10.1345/aph.1E397. Epub 2005 Mar. 22 (accessible via pubmed.ncbi.nlm.nih.gov/15784805/) and references cited therein.

Information on Mannopeptimycin can be found in the respective Wikipedia entry "Mannopeptimycin glycopeptide" (as at Jun. 10, 2020) and in H. He Appl Microbiol Biotechnol. 2005 June; 67 (4): 444-52. doi: 10.1007/s00253-004-1884-z. Epub 2005 Feb. 9 (accessible via pubmed.ncbi.nlm.nih.gov/15702316/) and references cited therein.

Information on Lincomycin (and Clindamycin) can be found in the respective Wikipedia entry (as at Jun. 10, 2020) and in J. Spízek and T. Rezanka Appl Microbiol Biotechnol. 2004 May; 64 (4): 455-64. doi: 10.1007/s00253-003-1545-7. Epub 2004 Feb. 5. (accessible via pubmed.ncbi.nlm.nih.gov/14762701/) and references cited therein.

Information on Pirlimycin can be found in the respective Wikipedia entry (as at Jun. 10, 2020) and in R. D. Birkenmeyer et al. J Med Chem. 1984 February; 27 (2): 216-23. doi: 10.1021/jm00368a020. (accessible via pubmed.ncbi.nlm.nih.gov/6363698/) and references cited therein.

6.8. Pharmaceutical Compositions 6.8.1. Afabicin Compositions

Afabicin can be administered orally, topically, transdermally or parenterally, including especially intravenous administration. Depending on the type of administration, the formulation will be adapted in a suitable manner. Co-pending European patent application No. 19 157 255.1, filed on Feb. 14, 2019 and associated international patent application PCT/EP2020/053882, filed on Feb. 14, 2020, describe suitable formulations designed for oral administration. The formulations described in this patent application may also be used for practicing the present invention. The disclosure of this application is therefore incorporated by reference in its entirety into the present application.

In particular, Afabicin formulations for oral administration, are preferably solid formulations selected from tablets and capsules. It is also preferred that such formulations contain a histidine compound. This may be histidine itself or a pharmaceutically acceptable salt of histidine. According to a particularly preferred embodiment, a tablet is employed which contains an internal phase (i.e. intragranular phase) and an external phase (i.e. extragranular phase), wherein Afabicin is contained mainly or exclusively in the internal part. The histidine compound is preferably present also in the internal phase only.

The Afabicin formulations for oral administration preferably contain further pharmaceutically acceptable excipients including one or more selected from binders, diluents, surfactants, disintegrants and the like. For the binder component it is preferred to select the binder from the group consisting of povidone (polyvinylpyrrolidone), copovidone (Poly(1-vinylpyrrolidone-co-vinyl acetate)), hydroxy propyl cellulose, hydroxyl propyl methyl cellulose, hydroxyethyl cellulose, methyl cellulose, microcrystalline cellulose, poloxamer (a block copolymer with a first poly(ethylene oxide) block, a second and central poly(propylene oxide) block and a third poly(ethylene oxide) block), polyethylene glycol, magnesium aluminosilicate, gelatin, acacia, alginic acid, carbomer (e.g. carbopol), carrageenan, dextrin, dextrates (a purified mixture of saccharides developed from the controlled enzymatic hydrolysis of starch), dextrose, polydextrose, guar gum, hydrogenated vegetable oil, liquid glucose, maltose, sucrose, lactose, wax, maltodextrin, starch (pregelatinized and plain), hydroxypropyl starch, glyceryl behenate, glyceryl palmitostearate, polyethylene oxide, sodium alginate, ethycellulose, cellulose acetate phthalate, polymethacrylate, carboxymethyl cellulose sodium, polycarbophil, chitosan and mixtures thereof.

For the diluent component, it is preferred to select the diluent from the group consisting of mannitol, isomalt, lactose (including anhydrous or monohydrate forms), calcium phosphate (including dibasic and tribasic calcium phosphate), calcium carbonate, magnesium carbonate, magnesium oxide, calcium sulfate, sucrose, fructose, maltose, xylitol, sorbitol, maltitol, lactitol, trehalose, aluminium silicate, dextrose, cyclodextrin (native or modified), starch (pregelatinized or plain), maltodextrin, cellulose (microcrystalline, silicified microcrystalline), glucose, dextrin, dextrates (a purified mixture of saccharides developed from the controlled enzymatic hydrolysis of starch), dextrose, polydextrose, ammonium alginate, glyceryl behenate, glyceryl palmitostearate, sodium alginate, ethycellulose, cellulose acetate, cellulose acetate phthalate, polymethacrylate, chitosan and mixtures thereof.

For the surfactant component it is preferred to select the surfactant from the group consisting of sodium lauryl sulfate, poloxamer, sodium docusate, sodium deoxycholate, sorbitan esters, polyethylene oxide, polysorbate 20, polysorbate 40, polysorbate 60, polysorbate 80 (ethoxylated sorbitan esterified with fatty acids wherein the number indicates the number of repeating units of polyethylene glycol), sucrose esters of fatty acid, tyloxapol, lecithin and mixtures thereof.

For the disintegrant component it is preferred to select the disintegrant from the group consisting of crospovidone, sodium starch glycolate, sodium croscarmellose, magnesium aluminosilicate, colloidal silicon dioxide, sodium alginate, calcium alginate, pregelatinized starch, microcrystalline cellulose, methylcellulose, hydroxypropyl cellulose, calcium carboxymethylcellulose, sodium carboxymethylcellulose, alginic acid, guar gum, homo- and copolymers of (meth)acrylic acid and salts thereof such as polacrillin potassium, and mixtures thereof.

Moreover, it is preferred to rely on formulations that do not contain cellulose-based excipient (i.e. containing a cellulose-type backbone, wherein the hydroxyl groups of the cellulose backbone may be modified by variable substituent groups such as $C_{1-6}$ alkyl, hydroxyl-$C_{1-6}$ alkyl, carboxy-$C_{1-6}$ alkyl-(C=O)—$C_{1-6}$ alkyl. It is also preferred to avoid the use of starch materials as excipients similar to the description of cellulose materials above, starch materials are to be understood as materials having an amylose or amylopectin backbone structure, wherein hydroxyl groups may be modified as explained above.

If the Afabicin formulation is to be administered orally, it is particularly preferred to administer a tablet having an internal and an external phase, the individual phases having the following compositions.

Internal phase:
  48 to 52 wt % Afabicin Olamine,
  17 to 21 wt. % of histidine
  4.75 to 6.75 wt. % binder,
  4.0 to 6.0 wt % surfactant, and
  1.6 to 3.6 wt. % disintegrating agent,
And External Phase:
  10.5 to 14.5 wt % diluent, (this amount does not include histidine compound describe above)
  0.75 to 2.75 wt % disintegrant,
  0.1 to 0.7 wt % glidant, and
  2.0 to 4.0 wt % lubricant.

As far as other administration forms of Afabicin are concerned, there are no particular restrictions. In particular, Afabicin may be provided for topical administration, transdermal administration or parenteral administration (intravenously, intramuscularly or subcutaneously), wherein the respective formulations are not particularly restricted.

Topical Afabicin formulations may be in the form of creams, lotions, gels, ointments, pastes, suspensions, drops, foams, and solutions.

Transdermal Afabicin formulations may be wound dressings, transdermal patches.

Parenteral Afabicin formulation may be in the form or solutions, suspensions, gels, solids that may be reconstituted before injection (powders, freeze dried product) or antibiotic implants such as beads and/or spacers comprising Afabicin and optionally at least one further agent selected from the group consisting of lipopeptides, glycopeptides and lincosamides, such as Daptomycin and/or Vancomycin and/or Clindamycin.

Creams may be water-in-oil emulsions or oil-in-water emulsions or multi-layer emulsions. The creams may contain micelles, liposomes, solvents, oils, surfactants, solubilizers, conservatives, and/or penetration enhancers.

Gels may contain gelling agents, solubilizers, solvents, conservatives, penetration enhancers, and/or surfactants.

Ointments and pastes may contain solvents, rheology modifiers, surfactants, penetration enhancers, conservatives, oils, and/or waxes.

Solutions, suspensions, foams and drops may contain solvents, solubilizers, viscosity modifiers, conservatives, penetration enhancers, surfactants.

Formulations for parenteral administration, including intravenous, intramuscular or subcutaneous administration, may be provided in solid form in vials such that they can be diluted in a suitable solvent (e.g. water, aqueous NaCl solution, e.g. 0.9 wt. % NaCl solution, aqueous glucose solution, dextrose solution). The solid component may contain, in addition to the drug substance, buffer, solubilizer, stabilizer, bulking agent, osmotic agent, surfactant, and/or viscosity modifier. The formulation for parenteral administration may also be provided in liquid form, e.g. in an infusion bag or in a prefilled syringe. In this case, the same components as listed above may be present in the liquid formulation.

Further parenteral administration types are also conceivable, including in particular medical implants comprising Afabicin (and optionally the at least one further agent mentioned hereinabove and below such as most preferably Daptomycin and/or Vancomycin and/or Clindamycin) in the medical implant or in a coating on the medical implant.

In one embodiment, the parental administration type is an antibiotic implant that is provided to the patient with the sole purpose of releasing the antibiotic(s). The antibiotic implant can, for instance, comprise a bead of an inert material such as poly(methyl methacrylate) (PMMA) or calcium sulphate, which carries the Afabicin (and optionally the at least one further agent mentioned hereinabove and below such as most preferably Daptomycin and/or Vancomycin and/or Clindamycin) within its pores and/or on its surface. Alternatively, the antibiotic implant can comprise a mixture of a biodegradable matrix material like PLGA and Afabicin (and optionally the at least one further agent mentioned hereinabove and below such as most preferably Daptomycin and/or Vancomycin and/or Clindamycin). The mixed matrix releases the antibiotic(s) over time while the matrix material is degraded within the patient's body. This embodiment may be useful for therapeutic treatment of biofilm infections.

In another embodiment, the parenteral administration type is be a medical implant that is to be implanted for (other) therapeutic reasons, such as an artificial joint. In this embodiment, it is an option to provide the surfaces of such medical implants with a coating comprising Afabicin (and optionally the at least one further agent mentioned hereinabove and below such as most preferably Daptomycin and/or Vancomycin and/or Clindamycin). Such coatings may comprise a drug-containing layer and optionally further layers such as an adhesive layer underneath the drug-containing layer and/or a top layer for release control. These layers may contain functional polymers such as polyvinylidene fluoride, polyethylene, polypropylene, polydimethylsiloxane, parylene, polyamide, polytetrafluoroethylene, poly(methyl methacrylate), polyimide, and/or polyurethane in addition to the respective drugs. Alternatively, Afabicin (and optionally the at least one further agent mentioned hereinabove and below such as most preferably Daptomycin and/or Vancomycin and/or Clindamycin) may be adhered to the material of the medical implant directly or via a suitable spacer moiety. This embodiment may be useful for prophylaxis of biofilm infections.

The combination of Afabicin and the at least one further agent mentioned hereinabove and below such as most preferably Daptomycin and/or Vancomycin and/or Clindamycin may also be applied to medical instruments e.g. surgical instruments or sutures. This may prevent bacterial growth on said medical instrument. Said medical instrument may also deliver the combination of Afabicin and the at least one further agent mentioned hereinabove and below at a surgical site, or a wound site e.g. in the case of a suture.

The term medical instrument as used herein refers to any tool used in a medical setting for the diagnosis or treatment of patients e.g. surgical tools such as scalpels and forceps, scissors and sutures.

The term "medical instrument" as used herein encompasses dental instruments.

6.8.2. Compositions of the at Least One Further Agent

There is no particular restriction regarding the compositions to be used for administering the at least one further agent. Generally, the at least one further antibiotic agent may be administered in any form that is commercially available and/or has received marketing approval and/or is generally accepted by the medical practitioner as being safe and effective. It is convenient and therefore preferable to rely on compositions and administration forms of the respective agents that have been authorized and that are commercially available. For instance, Daptomycin and Vancomycin are typically administered intravenously. Any formulation suitable for injection or infusion may be employed.

These may contain the same components as listed above in connection with Afabicin. It is preferred to use the commercially available Cubicin® and Vancocin® formulations, respectively.

Daptomycin and/or Vancomycin may also be provided as a formulation for topical administration. There is no particular restriction regarding the type of topical formulation. Again, the information provided above with respect to topical Afabicin formulations applies in an analogous manner also to topical Daptomycin and/or Vancomycin formulations. Moreover, Daptomycin and/or Vancomycin may be provided in a gel for instancel as described in WO 2015/118496, the disclosure of which is incorporated by reference in its entirety.

Clindamycin is commercially available in different forms and for different administration types. All of these compositions may be used. The use of commercially available compositions is preferred but the present invention is not limited to the use of such commercial compositions.

Similar considerations apply also when using another one of the further agents described hereinabove and below. There is no limitation regarding the administration form, type of composition, excipients present in the composition and so forth.

6.8.3. Combination Compositions

If Afabicin and the at least one further antibiotic agent are to be administered via the same route, the antibiotic agents may also be incorporated into the same pharmaceutical composition. For instance, if Afabicin is to be administered intravenously, it may also be provided in the form of a composition that contains Afabicin and the at least one further agent such as, most preferably, Daptomycin and/or Vancomycin and/or Clindamycin together. This could be, for instance, a composition comparable with the commercial Cubicin® formulation. Said commercial Cubicin® formulation contains Daptomycin in powder form together with sodium hydroxide as the excipient. This solid formulation is provided in the form of a vial for reconstitution with sodium chloride 9 mg/ml (0.9%) solution. A combined formulation may thus consist of Daptomycin, Afabicin and sodium hydroxide as well as optional further excipients (in solid form from reconstitution) or as a solution of these components in 0.9% sodium chloride solution.

Similarly, it is possible to use a combined formulation for injection that contains Afabicin and Vancomycin or Clindamycin, which is based on the commercial Vancocin® formulation or one of the commercially available Clindamycin formulations.

In another embodiment, the composition comprising a combination of Afabicin and the at least one further agent such as Daptomycin and/or Vancomycin and/or Clindamycin is a composition for topical administration and in particular a topical composition of the same type as described above in connection with Afabicin compositions and Daptomycin compositions, such as a gel composition. According to one specific embodiment, such topical compositions may be gel compositions containing Afabicin and the at least one further agent, most preferably Daptomycin and/or Vancomycin and/or Clindamycin. Such gels are advantageously administered directly into an open wound around the implant to ideally provide direct access to the biofilm.

6.9. Infections Involving Biofilm

6.9.1. *Staphylococcus* Types

The combination treatments of the present invention can be used for treating any biofilm infection and preferably any biofilm infection containing or consisting of any specific *staphylococcus* species including, for instance, the following species:

*Staphylococcus* species resistant to antibiotics commonly used to treat infections caused by gram-positive bacteria including but not limited to β-lactams such us penicillins (e.g. oxacillin, ampicillin) and cephalosporins (e.g. cefazolin, ceftarolin), vancomycin, linezolid, clindamycin, rifampicin, Daptomycin, fluoroquinolones such as levofloxacin and ciprofloxacin, trimethoprim/sulfamethoxazole, fosfomycin, fusidic acid, tigecycline and tetracyclines such as doxycycline, and dalbavancin Multidrug resistant *Staphylococcus* strains

*Staphylococcus aureus*

Community-acquired *Staphylococcus aureus*

Hospital-acquired *Staphylococcus aureus*

Methicillin-susceptible *Staphylococcus aureus* (MSSA)

Methicillin-resistant *Staphylococcus aureus* (MRSA)

*Staphylococcus aureus* strains resistant to antibiotics commonly used to treat infections caused by gram-positive bacteria including but not limited to β-lactams such us penicillins (e.g. oxacillin, ampicillin) and cephalosporins (e.g. cefazolin, ceftarolin), vancomycin, linezolid, clindamycin, rifampicin, Daptomycin, fluoroquinolones such as levofloxacin and ciprofloxacin, trimethoprim/sulfamethoxazole, fosfomycin, fusidic acid, tigecycline and tetracyclines such as doxycycline, and dalbavancin Multidrug resistant *Staphylococcus aureus* strains Coagulase negative Staphylococci (CoNS)

Coagulase negative Staphylococci strains resistant to antibiotics commonly used to treat infections caused by gram-positive bacteria including but not limited to β-lactams such as penicillins (e.g. oxacillin, ampicillin) and cephalosporins (e.g. cefazolin, ceftarolin), vancomycin, linezolid, clindamycin, rifampicin, Daptomycin, fluoroquinolones such as levofloxacin and ciprofloxacin, trimethoprim/sulfamethoxazole, fosfomycin, fusidic acid, tigecycline, and tetracyclines such as doxycycline, and dalbavancin Multidrug resistant CoNS strains

*Staphylococcus epidermidis*

Methicillin-resistant *Staphylococcus epidermidis* (MRSE)

Methicillin-susceptible *Staphylococcus epidermidis* (MSSE)

*Staphylococcus epidermidis* strains resistant to antibiotics commonly used to treat infections caused by gram-positive bacteria including but not limited to β-lactams such us penicillins (e.g. oxacillin, ampicillin) and cephalosporins (e.g. cefazolin, ceftarolin), vancomycin, linezolid, clindamycin, rifampicin, Daptomycin, fluoroquinolones such as levofloxacin and ciprofloxacin, trimethoprim/sulfamethoxazole, fosfomycin, fusidic acid, tigecycline, and tetracyclines such as doxycycline, and dalbavancin Multidrug resistant *Staphylococcus epidermidis* strains

*Staphylococcus haemolyticus*
*Staphylococcus lugdunensis*
*Staphylococcus simulans*
*Staphylococcus hominis*
*Staphylococcus arlettae*
*Staphylococcus auricularis*
*Staphylococcus capitis*
*Staphylococcus caprae*
*Staphylococcus cohnii*
*Staphylococcus equorum*
*Staphylococcus gallinarum*
*Staphylococcus jettensis*
*Staphylococcus kloosii*
*Staphylococcus lentus*
*Staphylococcus massiliensis,*
*Staphylococcus pasteuri*
*Staphylococcus pattenkoferi*
*Staphylococcus petrasii*
*Staphylococcus saccharolyticus*
*Staphylococcus saprophyticus*
*Staphylococcus schleiferi*
*Staphylococcus sciuri*
*Staphylococcus succinus*
*Staphylococcus vitulinus*
*Staphylococcus warneri*
*Staphylococcus xylosus*

In specific embodiments, the *staphylococcus* bacterium is selected from *Staphylococcus aureus* and CoNS such as *S. epidermidis*. This includes also all antibiotic-resistant strains, including but not limited to MRSA, MRSE, and strains resistant to rifampicin.

Of course, the combination treatment of the present invention can also be used for treating biofilm-mediated bacterial infections including two or more *staphylococcus* species. Similarly, the biofilm-mediated infection to be treated may include *staphylococcus* species together with other microorganisms (e.g. bacteria, fungi). In such cases, it may be advantageous to additionally use one or more further antibiotic agents suitable for the treatment of the additionally present microorganisms. This is important especially in those cases, in which the additionally present microorganisms are neither susceptible to treatment with Afabicin, nor to treatment with Daptomycin and/or Vancomycin.

6.9.2. Sites and Types of Infection with Biofilm

Biofilms may form at various sites of the human body including for instance native surfaces of human body parts (dental materials, bones, etc.) or foreign surfaces (medical implants e.g. contact lenses, prosthetic joints etc.). By consequence, there is a variety of infections known that may involve biofilms and especially biofilms that contain *staphylococcus* bacteria. These include the following:

A medical implant associated infection
osteomyelitis;
infections in cystic fibrosis patients;
pleuropulmonary infections such as *pneumoniae*, preferably wherein the
pleuropulmonary infection is chronic, and more preferably wherein the
pleuropulmonary infections is obstructive pulmonary disease;
endocarditis and preferably wherein the endocarditis is native valve endocarditis;
wound infections, preferably wherein said wound infections are chronic;
mastitis;
sinusitis, preferably wherein said sinusitis is chronic;
otitis media, preferably wherein said otitis media is chronic;
urinary tract infections;
tonsillitis, preferably wherein said tonsillitis is chronic;
laryngitis, preferably wherein said laryngitis is chronic;
infection associated with kidney stones;
biliary tract infections;
aerobic vaginitis;
septic thrombophlebitis;
infections associated with intracellular biofilms, for instance in Kupffer cells or in
tonsillar cells; and
colonization by *S. aureus* that predisposes the carrier to infections.

A medical implant associated infection can be an infection associated with any medical implant e.g. joint prostheses, orthopedic implants, heart valves, breast implants, ventricular shunts, pacemakers, defibrillators, ventricular-assisted devices, vascular grafts, endotracheal tubes, voice prostheses, soft tissue fillers (including permanent or semi-permanent tissue fillers), catheter-associated infections such as infections of central venous catheters, peripheral vascular catheters, peritoneal dialysis catheters, urinary catheters, keratitis due to biofilms on contact lenses. In particular the medical implant associated infection will be an infection associated with a medical implant that is a permanent indwelling devices, such as joint prostheses, orthopedic implants, heart valves, breast implants, ventricular shunts, pacemakers, defibrillators, ventricular-assisted devices, vascular grafts. Infections associated with a medical implant include infections listed above e.g. osteomyelitis which can just occur or whose occurance can be associated with a medical implant.

There are no particular restrictions concerning the sites and types of infection with biofilm, which are susceptible to treatment with the means and methods of the present invention. According to a preferred embodiment, the combination therapy of the present invention is used for treating prosthetic joint infections (PJI) associated with biofilms.

As noted above, all references to medical indications, which may or may not involve formation of biofilm, are intended to refer specifically to those forms of the respective medical indications, wherein biofilm is actually formed or presumed to be formed e.g. a prosthetic joint infection is intended to refer to a prosthetic join infection wherein biofilm is actually formed or presumed to be formed.

6.10. Method of Treatment

6.10.1. Dosages

As noted above, Afabicin may be used in the free acid form, in the form of the Olamine salt (or any other suitable salt form) or it is possible to use a combination of these different forms. Amount indications provided for Afabicin refer to the amount of the free acid form. If a salt of Afabicin is used, the amount must be correspondingly adjusted taking the higher molecular weight of the Afabicin salt into account. This is most easily done for an absolute amount indication in mg. The adjusted value may then be converted into a relative amount, if needed.

Typically, a single unit dose of the Afabicin formulation is administered at least once a day and administration two times a day is preferred. The daily dosage is determined by the physician taking severity of the infection, gender, weight, age and general condition of the patient into account. Typical daily dosages range for human from 120 to 480 mg. Typical daily dose is 120 or 240 mg twice a day, for a total of 240 to 480 mg per day. Hence, the present invention preferably relies on a unit dose strength of 120 mg or 240 mg of active pharmaceutical ingredient (calculated as Afabicin; e.g. if Afabicin Olamine is used, the preferred unit dose strength in terms of the total weight of Afabicin Olamine is 150 mg or 300 mg, respectively).

Daptomycin may be administered in a total daily dose of 0.1 to 10 mg/kg. More preferably, Daptomycin is administered in accordance with the guidance given in Section 4.2 of the Summary of Product Characteristics for Cubicin®, including especially the following administration details:
 cSSTI (complicated skin and soft-tissue infections) without concurrent SAB (*Staphylococcus aureus* bacteraemia): Cubicin 4 mg/kg is administered once every 24 hours for 7-14 days or until the infection is resolved (see section 5.1);
 cSSTI with concurrent SAB: Cubicin 6 mg/kg is administered once every 24 hours. The duration of therapy may need to be longer than 14 days in accordance with the perceived risk of complications in the individual patient.
 Known or suspected RIE (right-sided infective endocarditis) due to *Staphylococcus aureus*: Cubicin 6 mg/kg is administered once every 24 hours.

Vancomycin may be administered intravenously according to the following administration details:
 Patients aged 12 years and older: The recommended dose is 15 to 20 mg/kg of body weight every 8 to 12 h (not to exceed 2 g per dose). In seriously ill patients, a loading dose of 25-30 mg/kg of body weight can be used to facilitate rapid attainment of target trough serum vancomycin concentration.
 Infants and children aged from one month to less than 12 years of age: The recommended dose is 10 to 15 mg/kg body weight every 6 hours.

Clindamycin may be administered to adults intravenously or intramuscularly in daily dosages of 600 mg to 1.2 g for serious infections and 1.2 to 2.7 g for more severe infections, which are to be administered in two, three or four doses. For children, the administered dosage may be 15-25 mg/kg/day for serious infections and 25-40 mg/kg/day for more severe infections, which are to be administered in three or four doses.

If another antibiotic agent is used as the at least one further agent, i.e. another agent selected from lipopeptides, glycopeptides and lincosamides, it is recommended to select the dosage, administration type, frequency and any other relevant detail of the administration based on the established and/or authorized treatments with the respective agent.

Depending on the condition of the patient, it is possible to adjust the dosage, frequency of administration and/or duration of administration. For instance, it is possible to administer Daptomycin at a dosage of 4 mg/kg or 6 mg/kg at a frequency shorter than 24 h and/or for a duration longer than 7-14 days if the condition of the patient is serious or the treatment shows a slow response only. The dosage and administration frequency of Vancomycin or any other agent belonging to the group of lipopeptides, glycopeptides and lincosamides e.g. Daptomycin or Clindamycin may also be adjusted as required depending on the condition of the individual patient.

6.10.2. Administration Type

Afabicin can be administered orally, topically, transdermally or parenterally, including especially intravenous administration. If the active metabolite Debio 1452 is used as the Afabicin compound, this drug can be administered orally or topically.

There is no particular limitation for the at least one other agent selected from lipopeptides, glycopeptides and lincosamides. Any administration suitable for the agent of interest may be used. Authorized administration forms are preferred, especially if corresponding pharmaceutical compositions are commercially available. For instance, Daptomycin and Vancomycin are typically administered intravenously. However, topical administration forms such as gels are known. It is possible in accordance with the present invention to administer Daptomycin and/or Vancomycin intravenously, topically or by means of a combination of both. If further administration forms of Daptomycin and/or Vancomycin are developed in the future, it will also be possible to rely on such further administration forms for practicing the invention. For instance, it is conceivable to administer Afabicin and/or Daptomycin and/or Vancomycin in the form of a coating on the surface of a medical implant or in or on an antibiotic implant. Similar considerations apply also to the other agents belonging to the group of lipopeptides, glycopeptides and lincosamides.

If the patient is treated using algorithm involving different stages, it is possible to administer Afabicin in a first stage intravenously and in a second stage orally (or vice versa). The stages can also be repeated in the same or a different sequence. In such multi-stage treatments, the administration of the at least one other agent is not particularly limited except that it is restricted to the administration forms that are available or at least suitable for this drug.

In such multi-stage treatments, the intravenous or oral administration may be replaced or supplemented by other administration routes or their combinations (e.g. topical administration of Afabicin and/or topical administration of Daptomycin and/or topical administration of Vancomycin and/or topical administration of Clindamycin).

6.10.3. Use of Further Drugs

Additional drugs may also be used in addition to the drug combinations of the present invention as specified by the appended claims. There is, in principle, no particular limitation on the additional drugs that can be used. According to preferred embodiments, the further drugs (or co-drugs) are selected from antibiotic compounds. Suitable co-drugs are listed for instance in paragraphs- and claims 32-34 of WO 2013/190384 A. Specific co-drugs, including those mentioned in WO 2013/190384 A, are listed below.

Possible co-drugs include other FabI inhibitors, other antibiotic agents or antibacterial agents as described below.

Non-limiting examples of antibiotic agents that may be used as co-drugs include cephalosporins, quinolones and fluoroquinolones, penicillins, penicillins and beta lactamase inhibitors, carbepenems, monobactams, macrolides and lipoglycopeptides, rifamycin, oxazolidonones, tetracyclines, aminoglycosides, streptogramins, sulfonamides, and others. Each family comprises many members.

Cephalosporins can be further categorized by generation. Suitable non-limiting examples of cephalosporins by generation include the following. Examples of cephalosporins—First generation compounds include Cefadroxil, Cefazolin, Cefalexin, Cefalothin, Cefapirin and Cephradine. Second generation compounds include Cefaclor, Cefamandole, Cefonicid, Cefotetan, Cefoxitin, Cefprozil, Ceftmetazole, Cefuroxime, Cefuroxime axetil, and Loracarbef. —Third generation include Cefdinir, Ceftibuten, Cefditoren, Cefetamet, Cefbodoxime, Cefprozil, Cefuroxime (axetil), Cefuroxime (sodium), Cefoperazone, Cefixime, Cefotaxime, Cefpodoxime proxetil, Ceftazidime, Ceftizoxime, Cefcapene, Cefdaloxime, Cefmenoxime, Cefpiramide, and Ceftriaxone. Fourth generation compounds include Cefepime. Fifth generation compounds include Ceftaroline fosamil, Ceftolozane and Ceftobiprole.

Non-limiting examples of suitable quinolones and fluoroquinolones include Cinoxacin, Ciprofloxacin, Enoxacin, Gatifloxacin, Grepafloxacin, Levofloxacin, Lomefloxacin, Besifloxacin, Finafloxacin, Moxifloxacin, Nalidixic acid, Norfloxacin, Ofloxacin, Sparfloxacin, Trovafloxacin, Oxolinic acid, Gemifloxacin, Perfloxacin and Nemonoxacin and Novobiocin.

Non-limiting examples of suitable penicillins include Amoxicillin, Ampicillin, Bacampicillin, Carbenicillin Indanyl, Mezlocillin, Piperacillin, and Ticarcillin.

Non-limiting examples of suitable penicillins and beta lactamase inhibitors include Amoxicillin-Clavulanic Acid, Ampicillin-Sulbactam, Benzylpenicillin, Cloxacillin Dicloxacillin, Methicillin, Oxacillin, Penicillin G (Benzathine, Potassium, Procaine), Penicillin V, Piperacillin+Tazobactam, Ticarcillin+Clavulanic Acid, and Nafcillin.

Non-limiting examples of suitable carbepenems include Doripenem, Ertapenem, Imipenem-Cilastatin and Meropenem. A non-limiting example of a suitable monobactam includes Aztreonam. Non-limiting examples of suitable macrolides and lincosamines include Azithromycin, Clarithromycin, Dirithromycin, Erythromycin, Flurithromycin, Josamycin, Midecamycin, Miocamycin, Oleandomycin, Rokitamycin, Roxithromycin, Spiramycin, Tylosin, Ketolides and Troleandomycin. Non-limiting examples of suitable rifampins include Rifabutin, Rifampin, and Rifapentine. A non-limiting example of suitable oxazolidonones includes Linezolid, Eperezolid, Posizolid, Radelozid, Ranbezolid, Sutezolid, Tedizolid. Non-limiting examples of suitable tetracyclines include Demeclocycline, Doxycycline, Metacycline, Minocycline, Oxytetracycline, Tetracycline, Clomocycline, Lymecycline, Meclocycline, Penimepicycline, Rolitetracycline, Tigecycline and Chlortetracycline.

Non-limiting examples of suitable aminoglycosides include Amikacin, Arbakacin, Gentamicin, Kanamycin, Sisomicin, Arbekacin, Neomycin, Netilmicin, Streptomycin, Tobramycin, Bekanamycin, Ribostamycin, Spectinomycin, Hygromycin B, Dihydrostreptomycin, Verdamicin, Astromicin and Paromomycin. A non-limiting example of suitable streptogramins includes Quinopristin+Dalfopristin, Pristinamycin and Virginiamycin.

Non-limiting examples of suitable sulfonamides include Mafenide, Silver Sulfadiazine, Sulfacetamide, Sulfadiazine, Sulfamethoxazole, Sulfasalazine, Sulfisoxazole, Trimethoprim-Sulfamethoxazole, Sulfamethizole, Sulfaisodimidine, Sulfamethizole, Sulfadimidine, Sulfapyridine, Sulfafurazole, Sulfanilamide, Sulfathiazole, Sulfathiourea, Sulfamoxole, Sulfadimethoxine, Sulfadoxine, Sulfalene, Sulfametomidine, Sulfamethoxydiazine, Sulfamethoxypyradazine, Sullfaperin, Sulfamerazine, Sulfaphenazole, Sulfamazone.

Non-limiting examples of suitable other antibiotic agents include Bacitracin, Chloramphenicol, Azidamfenicol, Thiamphenicol, Florfenicol, Retapamulin, Tiamulin, Valnemulin, Fusidic Acid, Colistimethate, Fosfomycin, Isoniazid, Methenamine, Metronidazole, Tinidazole, Omidazole, Mupirocin, Nitrofurantoin, Nitrofurazone, Nifurtoinol, Novobiocin, Polymyxin B, Spectinomycin, Tobramycin, Tigecycline, Trimethoprim, Brodimoprim, Tetroxoprim, Colistin, Polymyxin B, Gramicidin, Isioniazid, Teixobactin, Cycloserine, Capreomycin, Pyrazinamide, para-Aminosalicyclic acid, and Erythromycin ethylsuccinate+sulfisoxazole.

If it is decided to use a combination with one or more of such further drugs, the indications herein regarding administration form, dosage, etc. may need to be suitably adapted taking the characteristics of the further co-drug into account. The one or more further co-drugs mentioned above can be administered prior to, simultaneously with and/or after administration of the Afabicin-containing drug combination of the present invention.

According to another preferred embodiment of the present invention, no further antibiotic agent is used, i.e. the treatment involves administration of a drug combination consisting of Afabicin and at least one further antibiotic agent selected from lipopeptides, glycopeptides and lincosamides. According to yet another preferred embodiment of the present invention, the treatment involves administration of a drug combination of Afabicin and at least one further antibiotic agent selected from lipopeptides, glycopeptides and lincosamides, and optionally one or more further antibiotic agents as specified in this section, but excluding Rifampicin as a further antibiotic agent.

6.10.4. Timing of Administration

In most embodiments, the administration of the Afabicin-containing drug combination of the present invention should be started as early as possible and be continued for a sufficiently long period of time to ensure therapeutic success. The required treatment duration depends on the specific type of infection, the patient's general condition, age, comorbidities, etc. and it can be determined by the treating physician.

Some embodiments of the present invention pertain to the treatment of biofilm-mediated bacterial infections, and preferably biofilm-mediated staphylococcal bacterial infections, associated with medical implants (temporary or permanent indwelling medical devices) e.g. catheter-associated infections, prosthetic joint infections, or infections associated with soft tissue fillers. A preferred embodiment relates to the treatment of PJI. For these embodiments, the following scenarios and associated treatments may be considered for implementing the present invention:

(i) If the patient has a duration of symptoms of three weeks or less, or infection occurs within four weeks after implantation and if the medical implant is stable and if there is an absence of sinus tract, the treatment method may involve retention of the medical implant (prosthetic joint). In this case, it is preferred to remove necrotic tissue vie debridement. This operation is preferably followed by a first treatment phase in which the drug combination of the present invention is administered intravenously. This first treatment phase may have a duration of typically two to six weeks. Subsequently, depending on the patient's condition, the first treatment phase is advantageously followed by a second treatment phase in which the drug combination of the present invention is administered such that Afabicin is administered orally while the at least one further agent such as Daptomycin and/or Vancomycin and/or Clindamycin is administered intravenously. The duration of said second treatment phase depends on the patient's condition and may typically last from six to ten weeks. Shorter or longer treatment times are also conceivable. If the patient is in poor condition, it may also be considered to prolong the first treatment phase, for instance to ten or twelve weeks. Typically, the second treatment phase is equal or longer than the first treatment phase.

(ii) If the above conditions outlined under item (i) are not all simultaneously fulfilled, i.e. if the medical implant (prosthetic joint) is not stable and/or presence of sinus tract is observed, the medical implant (prosthetic joint) is preferably replaced.

(ii-1) If the tissue surrounding the medical implant (prosthetic joint) is intact or only slightly damaged, the replacement of the medical implant (prosthetic joint) may be performed in a one stage procedure. Subsequently, the two treatment phases as outlined above under item (i) follow.

(ii-2) If there is damaged soft tissue, abscess or sinus tract, it is preferable to perform a two stage exchange with a short interval between removal and implantation. Said short interval may typically range from two to four weeks. The above mentioned first treatment stage with the drug combination of the present invention takes place at least during this short interval. Implantation of the new medical implant (prosthetic joint) may be followed by another time period of the first treatment stage and, subsequently the second treatment stage or it may be followed solely by the second treatment stage.

If the biofilm is difficult to treat, the time period between removal and implantation may be prolonged, for instance such that after removal of the medical implant (prosthetic joint) there is a six week period of the first treatment stage followed by two weeks of no administration of any antibiotics, followed by implantation of the new medical implant (prosthetic joint) and subsequently further intravenous administration in accordance with the first treatment stage until culture results are determined.

(iii) If the patient is inoperable, debilitated or bedridden, it is appropriate to perform long term suppressive antimicrobial treatment using the drug combination of the present invention. In this case, both treatment/administration of the first treatment stage and of the second treatment stage described above are available and may be chosen by the medical practitioner depending on the specific circumstances of the case.

(iv) If no functional improvement is expected by exchanging the medical implant (prosthetic joint), it may be most appropriate to remove the medical implant (prosthetic joint) without replacement. This procedure may also be followed by treatment with the drug combination of the present invention, preferably including the treatment in two stages as out lined under item (i) above.

Figure 1:
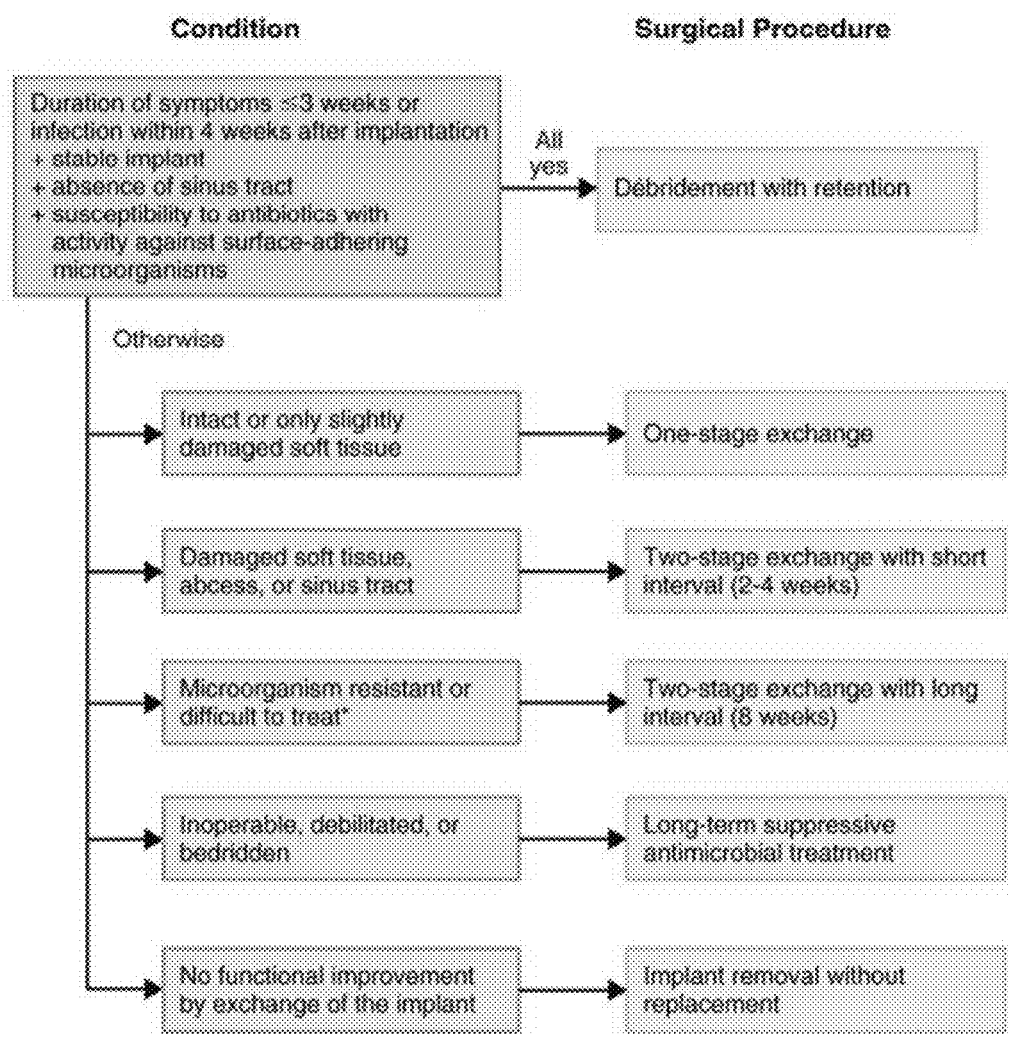
FIG. 1 is a schematic setting out treatment options for medical implant infections, and more specifically prosthetic join infections, based on different scenarios.
Figure 2:
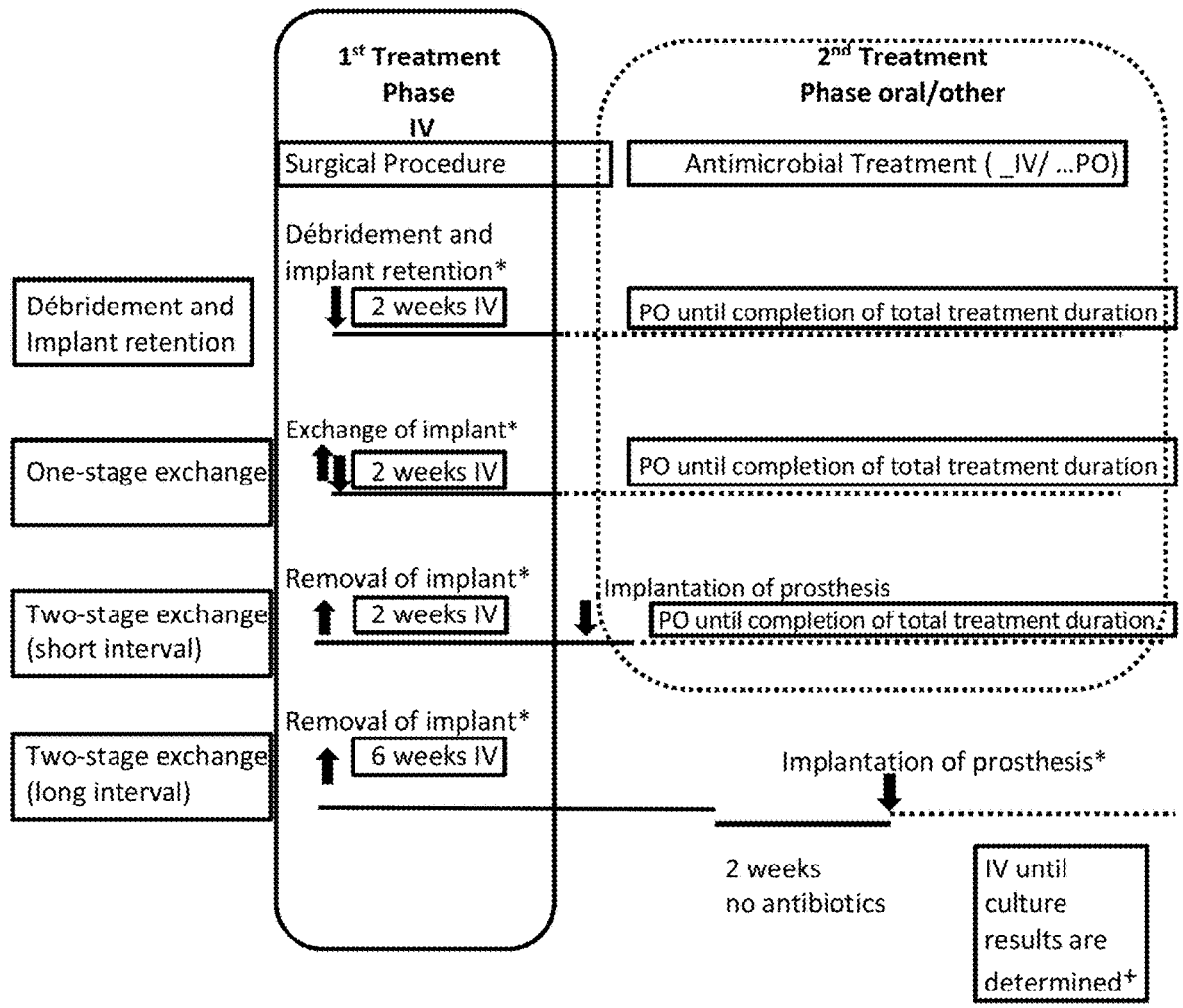
FIG. 2 is a schematic setting out treatment options for medical implant infections, and more specifically prosthetic join infections, based on different scenarios.

Treatment scenarios as detailed above are set out schematically in FIGS. 1 and 2.

In case of biofilm-mediated infections associated with medical implants other than prosthetic joints, the above general rules may also be applied in an analogous manner. Depending on the condition of the patient, the type and size of the medical implant, it may however be advantageous to adapt the time periods and sequence of phases mentioned above. The alternative treatment strategies may be performed in accordance with or be guided by recommendations included in Bennett J et al. eds. in Mandell, Douglas, and Bennett's Principles and Practice of Infectious Diseases, Vol 1. 8th ed. Philadelphia, PA; Elsevier 2015:1328-35.

6.11. Abbreviations

ACN Acetonitrile
AM Analytical method
BES bis-ethanolamine salt
bid twice daily (bis in die)
BLOQ Below the lower Limit of Quantification
C Calibration Standards
CFU colony-forming units
CSSTI complicated skin and soft-tissue infections
CV (%) Precision: Coefficient of variation=100×SD/mean
D or d day
DAP Daptomycin
DMSO Dimethyl sulfoxide
ESI Electrospray Ionization
FA Formic Acid
GLP Good Laboratory Practice
HED Human Equivalent Dose
IS Internal Standard
i.p. or IP intraperitoneal
ISR Incurred Sample Reproducibility
LC Liquid Chromatography
LC-MS/MS Liquid Chromatography-Tandem Mass Spectrometry
LLOQ Lower Limit of Quantification
LOD Limit of Detection
MeOH Methanol
MIC Minimal inhibitory concentration
MHA Mueller-Hinton agar
MRM Multiple Reaction Monitoring
MRSA Methicillin-resistant *Staphylococcus* (*S.*) *aureus*
MS/MS Tandem Mass Spectrometry
$NH_3$ Ammonium Hydroxyde
Nt not tested
Operational Instruction
o/n overnight
PBS Phosphate buffered saline
PJI Prosthetic joint infection
PK Pharmacokinetics
PO orally (per os)

QC Quality Control
QD or q.d. once daily (quaqua die)
qdam once daily in the morning (quaque die ante meridiem)
RIE right-sided infective endocarditis
RIF rifampicin
RT Room Temperature
S *Staphylococcus*
SA *Staphylococcus aureus*
SAB *Staphylococcus aureus* bacteraemia
SC Subcutaneous
SD Standard Deviation
SOC Standard of Care
SOP Standard Operating Procedure
TCF Tissue cage fluid
ULOQ Upper Limit of Quantification
UPLC Ultra-Performance Liquid Chromatography

7. EXAMPLES

7.1. Example 1: Evaluation of Activity of Debio 1450 BES as a Single Agent or in Combination with Antistaphylococcal Compounds Against 24 h and 72h Biofilms of MRSA in In Vivo Murine Model of Catheter Associated Infection Two experimental settings were used in this study to evaluate the treatment efficacies against early (24h) and/or mature (72h) MRSA catheter formed biofilms. Briefly, mice were anaesthetised by an IP injection of about 120 µl a mix of ketamine (50 mg/kg) and xylazine (10 mg/kg) (4 mL ketamine+2 mL xylazine+10 mL saline). Flank on the right side was shaved and then disinfected by 3 consecutive applications of betadine. A cutaneous and then subcutaneous (SC) incisions of 0.2 cm were made under sterile conditions and a 1 cm segment of polyurethane catheter (Ref. No. ES-04730 Arrow international) cut into 2 longitudinal fragments was inserted SC (into the incision and then pushed further under the skin, about 2 cm away from the incision). The inoculation was done simultaneously by placing 50 µl of the bacterial culture onto the catheter (106 CFU of ATCC 43300 MRSA strain). The incision was stitched up and disinfected. The day of the infection was referred to as Day0 (D0). To ensure that the study was conducted in sterile conditions from the start to the end of the experiment, non-infected mice (sentinel group) were included. Treatments started either on D1 or D3 post infection, corresponding to early (24h) or more mature (72h) catheter formed biofilms, respectively, and lasted for 5.5 days (D1-D6) or (D3-D8). In both 24 h and 72h biofilm settings, two groups of infected non-treated animals (Vehicle controls) were evaluated for bacterial counts: at baseline (24h or D1 [for 24-h biofilm] and 72h or D3 [for 72-h biofilm] post infection, i.e. time points corresponding to treatments initiations) and at the termination of treatment duration (D6 [for 24-h biofilm] and D8 [for 72-h biofilm] post infection). Post treatment CFUs were counted on D6 or D8 and results were expressed as $Log_{10}$ CFU/g of catheter (Mean±SEM). The limit of detection was determined as being 1 $Log_{10}$ CFU/g of catheter. Changes of CFU/g of catheter ($\Delta$ $Log_{10}$) from the baseline (D1 or D3 for 24-h and 72-h biofilm, respectively) and cure rates (corresponding to the percentage of mice without catheter-associated bacteria within a given treatment group) were also calculated. In vivo induction of antibiotic-resistant bacteria was analysed for all tested antibiotics.

Antibiotics doses were selected according to the effective doses in animals, which approximated the therapeutic human equivalent doses (HED) (Table 1).

TABLE 1

| | Dose level (mg/kg) | Dosing Route | Frequency | Therapeutic human equivalent dose (HED) | Comments |
|---|---|---|---|---|---|
| Debio 1450 BES | 50 | PO | BID | 240 mg BID PO or daily dose of 480 mg/day | Slightly higher than HED, was used for monotherapy and combination therapy (against 24-h & 72-h biofilms) |
| Daptomycin | 120 | IP | QD | >6 mg/kg QD IP | Tested in mono and combo therapy settings (against 24-h & 72-h biofilms) |
| Rifampicin | 30 | IP | BID | 10-15 mg/kg BID IP | Tested in mono and combo therapy settings (against 24-h & 72-h biofilms) |
| Vancomycin | 110 | SC | BID | 1 g IV every 12 hours, 2 to 3 g/day | Tested in mono and combo therapy settings (against 24-h & 72-h biofilms) |

Mice received antibiotics on D1, D2, D3, D4, D5 and D6 (only one administration at D6) or D3, D4, D5, D6, D7 and D8 (only one administration at D8). All antibiotics were administered BID IP, except Debio 1450 BES and Vancomycin, which were respectively given PO and SC. Daptomycin was tested as a once daily regimen to avoid tolerability issues. The antibiotics daily dosing was performed with a 10-12 hours interval between the two administrations. For combination therapy, antibiotics were administered simultaneously every 10-12 hours (the time required between the injection of the first antibiotic and the injection of the second antibiotic was less than 30 seconds per mouse).

In each sub-study, animals were randomly assigned to the antibiotic therapies or vehicle controls groups. Dose volumes were calculated according to individual body weight of each animal.

After blood collection, animals were sacrificed by cervical dislocation following anaesthesia. Two fragments of catheter per mouse were collected and were used for bacterial enumeration after sonication. Each fragment of catheter was individually washed under aseptic conditions in an Eppendorf tube (3 successive washing steps with 300 µl sterile saline). After the last wash, the catheter was suspended in 1 mL sterile saline, put in an ultrasonic bath (Advantage Lab) for 3 minutes at room temperature before being vigorously vortexed in order to detach all adherent bacteria from the catheter. Several successive dilutions of this suspension (undiluted, 10-2, 104) were cultured onto Chapman agar plates for 48 h at 37° C. If required, dilutions were repeated in case of unconvincing or inadequate results, the stability of the bacterial suspension at 4° C. having been previously verified. Bacterial colony counting was performed manually, a number of CFU/mL was determined and adjusted to g of catheter.

Overall, the study was conducted under sterile conditions, as no bacterial growth was observed from the catheters explanted from the sentinel mice. The bacterial load remained stable over the 5.5 days in the vehicle control groups (24h and 72h biofilms). Results of 5.5 days single and combination therapy of 24 h and 72h MRSA biofilms are summarized in Table 2. Daptomycin/Rifampicin was used as the standard of care (SOC) combination and served as a comparator during the entire study.

In the monotherapy setting, Rifampicin (30 mg/kg BID IP) showed the best activity among all the tested antibiotics against both the 24 h and 72h MRSA biofilms, resulting in a mean reduction of the initial MRSA load by $4.17\pm0.072$ $Log_{10}$ CFU/g and $2.98\pm0.113$ $Log_{10}$ CFU/g of catheter and cure rates of 39% and 8%, respectively. The SOC combination Daptomycin (120 mg/kg QD IP)±Rifampicin (30 mg/kg BID IP) showed the most prominent efficacy against 24 h and 72h biofilm and resulted in 58% and 25% cure rates and a mean reduction of the initial MRSA load by $5.00\pm0.069$ $Log_{10}$ CFU/g and $3.52\pm0.135$ $Log_{10}$ CFU/g of catheter, respectively.

Although Debio 1450 BES alone at 50 mg/kg BID PO exerted a relatively weak anti-biofilm effect, Debio 1450 BES (50 mg/kg BID PO)+Daptomycin (120 mg/kg QD IP) combination showed a comparable activity to the SOC of Rifampicin/Daptomycin. Debio 1450 BES/Daptomycin exhibited a 42%, 17% cure rates and reduced the initial MRSA load by $4.38\pm0.105$ $Log_{10}$ CFU/g and $3.36\pm0.121$ $Log_{10}$ CFU/g of catheter in the 24 h and 72h biofilm settings, respectively.

A second promising combination therapy against 24 h and 72 biofilms consisted of Debio 1450/Vancomycin ($3.69\pm0.118$ and $2.99\pm0.162$ mean $Log_{10}$ CFU/g of catheter reduction, 25% and 17% cure rate in the 24 h and 72h biofilm settings, respectively), while neither Debio 1450 nor Vancomycin was able to exhibit good anti-biofilm activities when used as single therapies.

Induction of resistance studies (determined after ex vivo bacterial exposure to 4×MIC of Debio 1452, Daptomycin, Rifampicin, or Vancomycin) in single and combination therapy showed no emergence of resistant mutants, regardless of the tested antibiotic or the biofilm setting model (24h or 72h biofilm).

TABLE 2

Summary of the bacterial load on catheters following 5.5-day treatment of BALB/c mice with single or combined antibiotics in 24 h or 72 h biofilm setting. Results are expressed as $Log_{10}$CFU/g of catheter at the end of treatment (D 6) and (D 8) for 24 h and 72 h biofilm, respectively, and $Log_{10}$CFU/g of catheter changes ($\Delta Log_{10}$) from the baselines before treatment (D 1 or D 3 for 24 h and 72 h biofilm, respectively). Mean ± standard error of the mean (SEM) are shown. Cure rates (CR, %) are presented. The statistical significance (p) of $Log_{10}$CFU/g of catheter (comparison of treated groups vs untreated control group at the end of treatment) was determined using ANOVA (completed by Bonferroni post hoc test)

| | Biofilm (24 h) | | | | Biofilm (72 h) | | | |
| --- | --- | --- | --- | --- | --- | --- | --- | --- |
| Treatment Groups | $Log_{10}$ CFU/g of catheter (D 6) Mean ± SEM | $\Delta Log_{10}$ CFU/g of catheter from (D 1) Mean ± SEM | p | CR (%) | $Log_{10}$ CFU/g of catheter (D 8) Mean ± SEM | $\Delta Log_{10}$ CFU/g of catheter from (D 3) Mean ± SEM | p | CR (%) |
| Untreated control | 5.95 ± 0.051 | −0.71 ± 0.051 | — | — | 6.47 ± 0.070 | −0.31 ± 0.07 | — | — |
| Debio 1450 50 mg/kg bid po | 4.31 ± 0.109 | −2.35 ± 0.109 | * | 8 | 5.75 ± 0.069 | −1.03 ± 0.069 | ns | 0 |
| Daptomycin 120 mg/kg qd ip | 3.02 ± 0.110 | −3.64 ± 0.110 | *** | 25 | 5.42 ± 0.104 | −1.37 ± 0.104 | ns | 0 |
| Combo 1 | 2.28 ± 0.105 | −4.38 ± 0.105 | *** | 42 | 3.42 ± 0.121 | −3.36 ± 0.121 | *** | 17 |
| Debio 1450 50 mg/kg bid po | 4.31 ± 0.109 | −2.35 ± 0.109 | * | 8 | 5.75 ± 0.069 | −1.03 ± 0.069 | ns | 0 |
| Vancomycin 110 mg/kg bid sc | 5.08 ± 0.105 | −1.59 ± 0.105 | ns | 0 | 4.84 ± 0.077 | −1.94 ± 0.077 | * | 0 |
| Combo 2 | 2.98 ± 0.118 | −3.69 ± 0.118 | *** | 25 | 3.79 ± 0.162 | −2.99 ± 0.162 | *** | 17 |
| Rifampicin 30 mg/kg bid ip | 2.50 ± 0.072 | −4.17 ± 0.072 | *** | 39 | 3.80 ± 0.113 | −2.98 ± 0.113 | *** | 8 |
| Daptomycin 120 mg/kg qd ip | 3.02 ± 0.110 | −3.64 ± 0.110 | *** | 25 | 5.42 ± 0.104 | −1.37 ± 0.104 | ns | 0 |
| Standard of care combo | 1.67 ± 0.069 | −5.00 ± 0.069 | *** | 58 | 3.26 ± 0.135 | −3.52 ± 0.135 | *** | 25 |

Combo 1. Debio 1450 (50 mg/kg bid po) + Daptomycin (120 mg/kg qd ip)
Combo 2. Debio 1450 (50 mg/kg bid po) + Vancomycin (110 mg/kg bid sc)
Standard of care combo. Daptomycin (120 mg/kg qd ip) + Rifampin (30 mg/kg bid ip)
* $p < 0.05$;  $p < 0.005$; * $p < 0.001$.
NS = not significant, NT = not tested.

In conclusion, Debio 1450 BES/Daptomycin and Debio 1450 BES/Vancomycin combinations showed a significant anti-biofilm activity, similar to the SOC Rifampicin/Daptomycin. Therefore, Debio 1450/Daptomycin and Debio 1450/Vancomycin combination could serve as a potent candidate for the limited treatment options for biofilm-mediated MRSA infections.

7.2. Example 2: Efficacy of Debio 1450 BES in the Mouse Tissue Cage Model of MRSA Infection The purpose of this study was to evaluate the efficacy of Debio 1450 BES alone and in combination with Daptomycin (DAP) in the mouse tissue cage model of implant-associated infections caused by methicillin resistant *Staphylococcus* (S.) *aureus* (MRSA). The efficacy against 24-h biofilm of *S. aureus* ATCC 43300 (MRSA) was investigated and compared to the standard of care combination of rifampicin (RIF) and DAP at the human equivalent doses. Employing a small initial inoculum (ca. 300 CFU/cage) together with a 24-h biofilm allowed to simulate clinical settings of an acute implant infection and/or surgical debridement.

The tissue cage model of prosthetic joint infections is very well-established and closely mimics the human prosthetic joint infections. This model is based on subcutaneous insertion of tissue cages followed by experimental infection of the foreign body by injection of bacterial inoculum into the cages.

In brief, one sterile polytetrafluorethylene (Teflon) cylinder (32×10 mm), perforated by 130 regularly spaced holes of 1 mm diameter (tissue cages; Angst-Pfister AG, Zürich) was aseptically implanted subcutaneously into the back of C57BL/6 mice (minimum weight 20 g). Experiments were started after complete wound healing (minimum 2 weeks after surgery). For the efficacy study presented here the cages in all animals were infected with around 300 colony-forming units (CFU) of the MRSA strain ATCC 43300 per cage and the biofilm were developed for 24 h before the beginning of the treatment.

The animals received antibiotic treatment i.p. (Debio 1450 BES and DAP) or sc (RIF) on day 1, 2, 3, 4, 5, and 6 (only the morning administration on day 6). One group received only 5% glucose and served as infected, untreated control group (vehicle). The treatment duration and antibiotic doses were chosen to be better able to compare the results of this study to the study of Example 1 above, where Debio 1450 BES (50 mg/kg)/DAP (120 mg/kg) combination against the 24-h MRSA biofilm showed 42% cure rate. Debio 1450 and vehicle were administered bid, and qdam on day 6. DAP and RIF were administered qdam. The 50 mg/kg dose of Debio 1450 BES was selected as the HED. The DAP dose of 100 mg/ml was chosen as it closely correlates with the human clinical dosage of 10 mg/kg once daily. The RIF dose of 25 mg/kg is among the most commonly used in the treatment of experimental biofilm infections.

Five to 6 days before infection, TCF is aspirated to ascertain the sterility of implanted cages by TCF plating on blood agar plates. TCF was aspirated and plated on day 1 (before treatment) to confirm the establishment of infection. In addition, the number of bacteria in TCF was determined on day 3 (before the first injection that day), on day 6 (before last treatment), and on day 9 (before explantation of the cages) to evaluate the treatment efficacy against planktonic bacteria. The mouse number and bacterial count for the given cage were reported to analyse the time course of antibacterial activity of the tested drugs. The efficacy against biofilm-embedded bacteria was assessed qualitatively and quantitatively following aseptic explantation of the tissue cages 3 days after the completion of treatment. The 3 days of resting period will help to avoid the antibiotic carryover effect. Upon explantation, cages were washed twice with phosphate buffered saline (PBS) (Lot #5060914) and immediately transferred into 5 mL 0.9% NaCl (Lot #L161619 or L162658). Following 30 s vortexing, sonication (3 min at 130 W), and an additional 30 s vortexing step the numbers of bacteria dispersed from biofilm was determined by plating. The sonicated cages were washed once with PBS, transferred into 5 mL TSB (Lot #0286463), and incubated for 48 h at 37° C., with an additional vortexing step after 24 h of incubation. After the incubation, tubes were vortexed again and bacterial regrowth was assessed visually. In addition, 100 μL of each culture was plated on blood agar plates to ascertain the regrowth. A positive culture was defined as a treatment failure. The efficacy of treatment against adherent bacteria is expressed as the cure rate (in percent), defined as the number of cages without growth divided by the total number of cages in the individual treatment group. In addition, single colonies from the re-growth plates were used to achieve the 0.5 McFarland. 100 μL of each 0.5 McFarland culture was plated on MHA plates containing the antibiotics corresponding to the treatment used (note: bacteria from mice treated with Debio 1450 were plated on plates containing Debio 1452). Growth conditions are shown in the following Table 3.

TABLE 3

| Treatment group: | Plate: |
|---|---|
| Debio 1450 50 mg/kg | MHA plates supplemented with: 4 × MIC Debio 1452 (0.008 μg/mL, 0.032 μg/mL, 0.0625 μg/mL, and 0.25 μg/mL)[1] of Debio 1452 |
| DAP 50 mg/kg | MHA plates: Etest for DAP |
| RIF 25 mg/kg | MHA plates supplemented with: 4 μg/mL RIF[2] |
| Debio 1450 50 mg/kg/ DAP 100 mg/kg | MHA plates supplemented with: 4 × MIC Debio 1452 (0.008 μg/mL. 0.032 μg/mL, 0.0625 μg/mL, and 0.25 μg/mL)[1] and MHA plates for Etest for DAP |
| RIF 25 mg/kg/ DAP 100 mg/kg | MHA plates supplemented with: 4 μg/mL RIF[2] and MHA plates for Etest for DAP |
| Vehicle (5% glucose) | MHA plates supplemented with: 4 × MIC Debio 1452 (0.008 μg/mL, 0.032 μg/mL, 0.0625 μg/mL, and 0.25 μg/mL)[1] |

[1] The range of Debio 1452 concentrations was used to cover the MIC of MRSA 43300 determined in-house (0.0625 μg/mL) and the historical data from the Sponsor (0.008 μg/mL).
[2] These concentrations reflect the CLSI susceptibility breakpoints.

Debio 1450 BES alone exerted only a moderate anti-biofilm effect with an adherent bacteria reduction from baseline of 3.81±1.15 log 10 CFU/mL (mean±SD, n=3) and 50% cure rate (n=6) (Table 4 and FIG. 3). A reduction of 3.91±0.98 log 10 CFU/mL (n=3) and cure rate of 33% (n=6) was observed for this antibiotic. As expected from its known anti-biofilm effect, rifampicin was the most active amongst the tested monotherapies (3.37±0 log 10 CFU/mL (n=3) and cure rate of 100% (n=5)).

Debio 1450 BES/Daptomycin combination showed enhanced activity than either compound alone, reducing the biofilm by 4.48±0 log 10 CFU/mL (n=3) and eradicating the infection in 83% of animals (n=6, treatment failure observed only in 1 animal). The anti-biofilm activity of Debio 1450 BES/Daptomycin combination was comparable to the standard of care rifampicin/Daptomycin (biofilm reduction of 4.48±0 log 10 CFU/mL (n=3) and 100% cure rate (n=5)). The level of adherent bacteria at day 9 was significantly lower in the animals treated with Debio 1450 BES/Daptomycin (p=0.0044, n=6, Kruskal-Wallis and Dunn's tests), rifampicin/Daptomycin (p=0.0014, n=5) and rifampicin (p=0.0014, n=5) compared to the vehicle Group.

Investigation of planktonic bacteria revealed that rifampicin and Daptomycin as monotherapy and in combination exerted bactericidal effect (i.e. mean reduction of bacterial load by ≥3 $Log_{10}$) on day 3 (i.e. after 2 days of treatment), whereas Debio 1450 BES and Debio 1450 BES/Daptomycin on day 6 (i.e. after 5 days of treatment). Since additional time points between day 1 and day 6 were not assessed, the exact time course of the bactericidal effect cannot be inferred. The results are summarized in Table 4 below.

(DAP) in the mouse tissue cage model of implant-associated infections caused by methicillin resistant *Staphylococcus* (S.) *aureus* (MRSA) at lower dosage and longer treatment duration than used in the previous study (Example 2). The efficacy against 24-h biofilm of *S. aureus* ATCC 43300 (MRSA) was investigated. Employing a small initial inoculum (ca. 300 CFU/cage) together with a 24-h biofilm allowed to simulate clinical settings of an acute implant infection and/or surgical debridement.

The Debio 1450 BES dose of 20 mg/kg BID reflects the most current HED of 240 mg BID obtained in the recent PK

TABLE 4

Effect of antibiotic treatment on planktonic and adherent bacteria. The reduction of planktonic and adherent bacterial fraction from baseline (day 1, before treatment) was determined by plating of tissue cage fluid (day 1, 3, 6 and 9) and medium after sonication of the explanted tissue cages (day 1 and day 9). Adherent bacteria regrowth following sonication and the cure rate are indicated; nt = not tested.

| | Planktonic | | | | | | | | | Adherent | | | | Cure rate |
|---|---|---|---|---|---|---|---|---|---|---|---|---|---|---|
| | day 3 | | | day 6 | | | day 9 | | | | | | | |
| | Δlog | Mean | SD | Δlog | Mea | SD | Δlog | Mea | SD | Δlog | Mea | SD | Regrowth | (%) |
| 5% glucose | 1.37 | 2.11 | 0.76 | 3.68 | 3.05 | 0.91 | 3.70 | 3.35 | 0.50 | nt | 2.92 | 0.17 | + | 0 |
| (200 μl; | 1.31 | | | 2.32 | | | 2.73 | | | nt | | | + | |
| i.p., 12 h) | 2.56 | | | 4.60 | | | 4.03 | | | 2.72 | | | + | |
| | 2.87 | | | 2.87 | | | 2.89 | | | 3.00 | | | + | |
| | 1.6 | | | 2.5 | | | 3.2 | | | 2.9 | | | + | |
| | 2.9 | | | 2.3 | | | 3.6 | | | 3.1 | | | + | |
| Debio 1450 | −1.42 | −2.62 | 1.50 | −3.24 | −4.45 | 1.18 | −5.85 | −3.90 | 1.70 | nt | −3.81 | 1.15 | − | 50 |
| (50 mg/kg; | −1.40 | | | −2.69 | | | −3.41 | | | nt | | | + | |
| i.p.; 12 h) | −2.10 | | | −5.64 | | | −1.32 | | | nt | | | + | |
| | −5.10 | | | −5.10 | | | −5.10 | | | −4.48 | | | − | |
| | −1.93 | | | −4.91 | | | −4.91 | | | −4.48 | | | − | |
| | −3.79 | | | −5.09 | | | −2.79 | | | −2.48 | | | + | |
| DAP | −2.41 | −3.10 | 1.65 | −5.72 | −4.91 | 1.27 | −1.07 | −3.60 | 2.74 | nt | −3.91 | 0.98 | + | 33 |
| (100 mg/kg; | −4.79 | | | −4.79 | | | −4.79 | | | nt | | | + | |
| i.p.; 24 h) | −0.67 | | | −2.46 | | | 0.73 | | | nt | | | + | |
| | −5.15 | | | −5.15 | | | −5.15 | | | −4.48 | | | − | |
| | −2.91 | | | −5.95 | | | −5.95 | | | −2.78 | | | + | |
| | −2.70 | | | −5.38 | | | −5.38 | | | −4.48 | | | − | |
| Debio 1450 | −2.00 | −2.68 | 0.46 | −5.60 | −5.53 | 0.44 | −0.38 | −4.66 | 2.14 | nt | −4.48 | 0 | + | 83 |
| (50 mg/kg; | −2.93 | | | −6.01 | | | −6.01 | | | nt | | | − | |
| i.p.; 12 h) + | −2.98 | | | −5.98 | | | −5.98 | | | nt | | | − | |
| DAP | −2.32 | | | −4.92 | | | −4.92 | | | −4.48 | | | − | |
| (100 mg/kg; | −2.62 | | | −5.11 | | | −5.11 | | | −4.48 | | | − | |
| i.p.; 24 h) | −3.22 | | | −5.56 | | | −5.56 | | | −4.48 | | | − | |
| RIF | −4.08 | −4.53 | 1.37 | −4.08 | −4.53 | 1.37 | −4.08 | −4.53 | 1.37 | nt | −3.37 | 0 | − | 100 |
| (25 mg/kg; | −6.73 | | | −6.73 | | | −6.73 | | | nt | | | − | |
| s.c.; 24 h) | −3.5 | | | −3.5 | | | −3.5 | | | −3.4 | | | − | |
| | −3.4 | | | −3.4 | | | −3.4 | | | −3.4 | | | − | |
| | −4.9 | | | −4.9 | | | −4.9 | | | −3.4 | | | − | |
| DAP | −6.15 | −5.64 | 0.62 | −6.15 | −5.64 | 0.62 | −6.15 | −5.62 | 0.72 | nt | −3.37 | 0 | − | 100 |
| (100 mg/kg; | −5.57 | | | −5.75 | | | no TCF | | | nt | | | − | |
| i.p.; 24 h) + | −4.6 | | | −4.6 | | | −4.6 | | | −3.4 | | | − | |
| RIF | −6.1 | | | −6.1 | | | −6.1 | | | −3.4 | | | − | |
| (25 mg/kg; | −5.6 | | | −5.6 | | | −5.6 | | | −3.4 | | | − | |
| s.c., 24 h) | | | | | | | | | | | | | | |

A graphical representation of the results is given in FIG. 3. Ex vivo investigation of in vivo treatment-induced resistance revealed no decrease in susceptibility to respective antibiotics used as monotherapy and in combination.

In summary, the anti-biofilm activity of Debio 1450 BES/Daptomycin combination similar to the standard of care rifampicin/Daptomycin obtained in this study confirms the data observed in the mouse catheter-associated biofilm infection model (cf. Example 1 above).

7.3. Example 3: Efficacy of Debio 1450 BES in the Mouse Tissue Cage Model of MRSA Infection The purpose of this study was to evaluate the efficacy of Debio 1450 BES alone and in combination with Daptomycin studies (50 mg/kg BID was used in Example 2 based on the previous PK analysis). The dose of Daptomycin was also reduced from 100 mg/kg qdam (Example 2) to 50 mg/kg qdam, a dose that was previously used in this model and that represents a lower clinically recommended dose range. The treatment duration of 11 days was selected to compensate lowering of the dose of Debio 1450 BES (5.5-day treatment was used in Example 2) and is in line with the prolonged antibiotic therapy applied in patients with prosthetic joint infections.

The same mouse tissue cage model was employed as described in Example 2 above. The animals received antibiotic treatment i.p. on day 1 post-infection through day 11. One group received only 5% glucose and served as infected, untreated control group (vehicle). The treatment duration and antibiotic doses were chosen to be better able to compare the results of this study to the study of Example 1 (the mouse catheter-associated biofilm infection model), where Debio 1450 BES (50 mg/kg)/DAP (120 mg/kg) combination against the 24-h MRSA biofilm showed 42% cure rate. Debio 1450 BES and vehicle were administered bid, and DAP was administered qdam. In the present study we investigated the efficacy of lower dosage in a prolonged treatment duration.

Five to 6 days before infection, TCF was aspirated to ascertain the sterility of implanted cages by TCF plating on blood agar plates. TCF was aspirated and plated on day 1 (before treatment) to confirm the establishment of infection. In addition, the number of bacteria in TCF was determined on day 3 (before the first injection that day), on day 6, day 9 and on day 11 (before last treatment), and on day 14 (before explantation of the cages) to evaluate the treatment efficacy against planktonic bacteria. The mouse number and bacterial count for the given cage is reported to analyse the time course of antibacterial activity of the tested drugs. The efficacy against biofilm-embedded bacteria is assessed qualitatively and quantitatively following aseptic explantation of the tissue cages 3 days after the completion of treatment. The 3 days of resting period helped to avoid the antibiotic carryover effect. Upon explantation, cages were washed twice with phosphate buffered saline (PBS) (Lot #5060914) and immediately transferred into 5 mL 0.9% NaCl (Lot #L171095). Following 30 s vortexing, sonication (3 min at 130 W), and an additional 30 s vortexing step the numbers of bacteria dispersed from biofilm was determined by plating. The sonicated cages were washed once with PBS, transferred into 5 mL TSB (Lot #0286463), and incubated for 48 h at 37° C., with an additional vortexing step after 24 h of incubation. After the incubation, tubes were vortexed again and bacterial regrowth was assessed visually. In addition, 100 μL of each culture was plated on blood agar plates to ascertain the regrowth. A positive culture is defined as a treatment failure. The efficacy of treatment against adherent bacteria is expressed as the cure rate (in percent), defined as the number of cages without growth divided by the total number of cages in the individual treatment group. In addition, single colonies from the re-growth plates were used to achieve the 0.5 McFarland. 100 μl of each 0.5 McFarland culture was plated on MHA plates containing the antibiotics corresponding to the treatment used (note: bacteria from mice treated with Debio 1450 will be plated on plates containing Debio 1452). Growth conditions are shown in the following Table 5.

TABLE 5

| Treatment group: | Plate: |
|---|---|
| Debio 1450 BES (20 mg/kg) | MHA plates supplemented with: 4 × MIC Debio 1452 (0.032 μg/mL) and 8 × MIC Debio1452 (0.0625 μg/mL) |
| DAP (50 mg/kg) | Blood agar plates: Etest for DAP |
| Debio 1450 BES (20 mg/kg)/ DAP (50 mg/kg) | MHA plates supplemented with: 4 × MIC Debio 1452 (0.032 μg/mL and 8 × MIC Debio1452 (0.0625 μg/mL,) and blood agar plates for Etest for DAP |
| Vehicle (5% glucose) | MHA plates supplemented with: 4 × MIC Debio 1452 (0.032 μg/mL and 8 × MIC Debio1452 (0.0625 μg/mL,) and blood agar plates for Etest for DAP |

Debio 1450 BES alone exerted a good anti-biofilm effect with an adherent bacteria reduction from baseline of 4.35±2.5 log 10 CFU/mL (mean±SD) and 83% cure rate (n=6) (Table 6 and FIG. 4). In line with a previous report on the activity of Daptomycin in this model, a reduction of 3.15±2.74 log 10 CFU/mL and cure rate of 50% (n=6) was observed for this antibiotic. Debio 1450 BES/Daptomycin combination showed enhanced activity than either compound alone, reducing the biofilm by 5.13±0.99 log 10 CFU/mL and eradicating the infection in 100% of animals (n=6). These cure rates were slightly higher than in the study of Example 2, where Debio 1450 BES and Daptomycin monotherapy, Debio 1450 BES/Daptomycin combination eradicated infection in 50%, 33%, and 83% (n=6) animals, respectively. In comparison to the vehicle group, the level of adherent bacteria at day 14 was significantly lower in the animals treated with Debio 1450 BES (p=0.0069, n=6, Kruskal-Wallis and Dunn's tests) and Debio 1450 BES/Daptomycin (p=0.0011, n=6), but not with Daptomycin (p=0.00631, n=6).

Investigation of planktonic bacteria revealed that Debio 1450 BES and Daptomycin as monotherapy and in combination exerted bactericidal effect (i.e. mean reduction of bacterial load by ≥3 $Log_{10}$) on day 6 (i.e. after 5 days of treatment). Since additional time points between day 1 and day 6 were not assessed, the exact time course of the bactericidal effect cannot be inferred.

TABLE 6

Effect of antibiotic treatment on planktonic and adherent bacteria. The reduction of planktonic and adherent bacterial fraction from baseline (day 1, before treatment) was determined by plating of tissue cage fluid (day 1, 3, 6, 9, 11 and 14) and medium after sonication of the explanted tissue cages (day 1 and day 14). Adherent bacteria regrowth following sonication and the cure rate are indicated.

| | | | Planktonic | | | | | | | |
|---|---|---|---|---|---|---|---|---|---|---|
| Results: | | | day 3 | | | day 6 | | | day 9 | |
| AKW109 | | | Δlog from | | | Δlog from | | | Δlog from | day 11 |
| part 1 & 2 | SD | Mean | baseline | SD | Mean | baseline | SD | Mean | baseline | SD Mean |
| 5% glucose (200 μl; i.p., 24 h) | 1 | 2.2 | 3.20 1.56 3.64 1.21 1.3 | 1 | 3.22 | 4.08 1.93 5.01 2.60 2.5 | 1 | 3.54 | 3.61 2.96 5.31 2.93 2.9 | 1  4.14 |

TABLE 6-continued

Effect of antibiotic treatment on planktonic and adherent bacteria. The reduction of planktonic and adherent bacterial fraction from baseline (day 1, before treatment) was determined by plating of tissue cage fluid (day 1, 3, 6, 9, 11 and 14) and medium after sonication of the explanted tissue cages (day 1 and day 14). Adherent bacteria regrowth following sonication and the cure rate are indicated.

| | | | | | | | | | | |
|---|---|---|---|---|---|---|---|---|---|---|
| Debio 1450 (20 mg/kg; i.p.; 12 h) | 1 | −3 | −1.46 −3.68 −2.22 −3.33 −3.03 −2.37 | 0 | −3.50 | −3.1 −3.7 −4.2 −3.3 −3 −3.7 | 1 | −4.10 | −3.1 −3.7 −6.2 −3.3 −3 −5.3 | 1 | −4.10 |
| DAP (50 mg/kg; i.p.; 24 h) | 1 | −3 | −2.56 −2.18 −3.12 −2.06 −3.41 −3.62 | 0 | −3.33 | −2.7 −3.5 −3.5 −3.4 −3.4 −3.6 | 1 | −3.9 | −4.6 −5.5 −2.7 −3.4 −3.6 −3.6 | 1 | −3.73 |
| Debio 1450 (20 mg/kg; i.p.; 12 h) + DAP (50 mg/kg; i.p.; 24 h) | 1 | −3 | −1.72 −2.07 −2.60 −3.32 −3.82 −3.01 | 1 | −3.90 | −3.1 −3.7 −3.90 −3.3 −6.4 −3 | 1 | −4.5 | −5.1 −5 −3.90 −3.3 −6.4 −3 | 1 | −4.45 |

| Results: AKW109 part 1 & 2 | Planktonic day 11 Δlog from baseline | SD | Mean | day 14 Δlog from baseline | Adherent SD | Mean | Δlog from baseline | Regrowth | Cure rate (%) |
|---|---|---|---|---|---|---|---|---|---|
| 5% glucose (200 μl; i.p., 24 h) | 4.29 3.46 5.43 3.46 4.0 | 1 | 3.8 | no TCF 2.65 5.30 2.88 4.3 | 1.72 | 1.6 | 3.59 2.92 1.05 1.35 −0.8 | + + + + + | 0 |
| Debio 1450 (20 mg/kg; i.p.; 12 h) | −3.1 −3.7 −6.2 −3.3 −3 −5.3 | 2 | −3 | −3.1 −3.7 −0.2 −3.3 −3 −5.3 | 2.50 | −4 | −4.2 −4.2 0.43 −6 −6 −6 | − − + − − − | 83 |
| DAP (50 mg/kg; i.p.; 24 h) | −4.6 −2.9 −2.70 −3.4 −5.2 −3.6 | 2 | −2 | −4.6 −1.1 −1.5 −3.4 −0.6 −3.6 | 2.74 | −3 | −4.2 −0.3 0.24 −6 −2.5 −6 | − + + − + − | 50 |
| Debio 1450 (20 mg/kg; i.p.; 12 h) + DAP (50 mg/kg; i.p.; 24 h) | −5.1 −5 −3.90 −3.3 −6.4 −3 | 1 | −4 | −5.1 −5 −3.90 −3.3 −6.4 −3 | 0.99 | −5 | −4.2 −4.2 −4.2 −6 −6 −6 | − − − − − − | 100 |

A graphical representation of the results is given in FIG. 4. Ex vivo investigation of in vivo treatment-induced resistance revealed no decrease in susceptibility to respective antibiotics used.

In summary, the anti-biofilm activity of Debio 1450 BES/Daptomycin combination obtained in this study confirms the data observed in the previous study using this model as described in Example 2 above and the mouse catheter-associated biofilm infection model described in Example 1 above.

7.1. Example 4: Efficacy of Debio 1450 BES in the Mouse Tissue Cage Model of Staphylococcal Biofilm Infection The purpose of this study was to evaluate the efficacy of Debio 1450 BES in combination with Clindamycin or with Vancomycin and to compare it to the corresponding combinations of Rifampicin using the mouse tissue cage model of implant-associated infections. The efficacy against 24-h biofilm of S. aureus ATCC 29213 (methicillin-susceptible S. aureus [MSSA]) and of S. aureus ATCC 43300 (MRSA) was tested for combinations with Clindamycin and with Vancomycin, respectively.

The same mouse tissue cage model was employed as described in Example 3 above. The animals received antibiotic treatment on day 1 post-infection through day 11 (i.e. 11-day treatment) at a dosing regimen indicated in Table 7. The efficacy against biofilm-embedded bacteria was assessed quantitatively following aseptic explantation of the tissue cages 3 days after the completion of treatment. Upon explantation, cages were washed twice with phosphate buffered saline (PBS) and immediately transferred into 5 mL 0.9% NaCl. Following 30 s vortexing, sonication (3 min at 130 W), and an additional 30 s vortexing step the sonicated cages were washed once with PBS, transferred into 5 mL TSB, and incubated for 48 h at 37° C., with an additional vortexing step after 24 h of incubation. After the incubation, tubes were vortexed again and bacterial regrowth was assessed visually. A positive culture is defined as a treatment failure. The efficacy of treatment against adherent bacteria is expressed as the cure rate (in percent), defined as the number of cages without growth divided by the total number of cages in the individual treatment group.

The results are summarized in Table 7. The anti-biofilm activity (expressed as cure rate (%)) of Debio 1450 BES/Clindamycin and of Debio 1450 BES/Vancomycin combination was similar to the combination of Rifampicin/Clindamycin and Rifampicin/Vancomycin, respectively.

TABLE 7

Summary of cure rate following 11-day treatment of a 24-h staphylococcal biofilm in a mouse tissue cage model. The regrowth of staphylococci from tissue cages explanted on day 14 (i.e. 3 days post-end of treatment was determined. A positive bacterial culture was defined as a treatment failure. The efficacy of treatment against adherent bacteria is expressed as cure rate (in percent), defined as the number of cages without growth divided by the total number of cages in the individual treatment group.

| Treatment* (11-d) | Biofilm (24-h) | Cure rate No. of cages without re-growth/No. of cages total (%) |
|---|---|---|
| Debio 1450 | MSSA ATCC 29213 | 1/7 (14.3) |
| Rifampicin | | 7/7 (100) |
| Debio 1450 + Clindamycin | MSSA ATCC 29213 | 4/5 (80) |
| Rifampicin + Clindamycin | | 4/4 (100) |
| Debio 1450 + Vancomycin | MRSA ATCC 43300 | 4/5 (80) |
| Rifampicin + Vancomycin | | 4/4 (100) |

*Antibiotics were dosed as follows: Debio 1450 (20 mg/kg, IP BID), Rifampicin (25 mg/kg, SC QD), Clindamycin (300 mg/kg, IP BID), Vancomycin (110 mg/kg SC BID).

The invention claimed is:

1. A method of treating bacterial infections involving biofilm in a patient wherein the method comprises administering Afabicin or a pharmaceutically acceptable salt, hydrate, solvate or polymorph thereof in combination with at least one further agent or pharmaceutically acceptable salt, hydrate, solvate or polymorph thereof, selected from the group consisting of lipopeptides, glycopeptides and lincosamides, or a pharmaceutically acceptable salt, hydrate, solvate or polymorph thereof, to the patient, wherein the Afabicin, or a pharmaceutically acceptable salt, hydrate, solvate or polymorph thereof, is administered in a first stage intravenously and in a second stage orally.

2. The method according to claim 1, wherein the biofilm contains or consists of *staphylococcus* bacteria.

3. The method according to claim 2, wherein the *staphylococcus* bacteria are selected from the group consisting of:
Staphylococcus aureus,
Coagulase negative Staphylococci (CoNS),
Methicillin-susceptible or methicillin-resistant Staphylococci,
*Staphylococcus aureus* strains, or CoNS strains wherein said strains are resistant to one or more antibiotic, and
Multidrug resistant *Staphylococcus* strains.

4. The method according to claim 1, wherein the bacterial infection is associated with an open wound and/or wet wound and/or a wound with drainage in place.

5. The method according to claim 1, wherein the Afabicin or a pharmaceutically acceptable salt, hydrate, solvate or polymorph thereof in combination with the at least one further agent, or pharmaceutically acceptable salt, hydrate, solvate or polymorph thereof, is administered during a perioperative period.

6. The method according to claim 1, wherein the bacterial infection involves biofilm that contains *staphylococcus* bacteria resistant to rifampicin.

7. The method according to claim 1, wherein the bacterial infection involves biofilm that contains methicillin-resistant staphylococci.

8. The method according to claim 1, wherein the bacterial infection is selected from the group consisting of:
a medical implant associated infection,
osteomyelitis,
infections in cystic fibrosis patients,
pleuropulmonary infections,
endocarditis,
wound infections,
mastitis,
sinusitis,
otitis media,
urinary tract infections,
tonsillitis,
laryngitis,
infection associated with kidney stones,
biliary tract infections,
aerobic vaginitis,
septic thrombophlebitis,
infections associated with intracellular biofilms, and
colonization by *Staphylococcus aureus* that predisposes the patient to infections.

9. The method according to claim 1, wherein the bacterial infection is a medical implant associated infection and wherein the medical implant is a permanent indwelling device.

10. The method according to claim 1, wherein the bacterial infection is a medical implant associated infection.

11. The method according to claim 1, wherein the method includes a step of debridement in addition to the administration of Afabicin or a pharmaceutically acceptable salt, hydrate, solvate or polymorph thereof in combination with the at least one further agent, or pharmaceutically acceptable salt, hydrate, solvate or polymorph thereof.

12. The method according to claim 9, wherein said method includes a step of exchanging the medical implant in addition to the administration of Afabicin or a pharmaceutically acceptable salt, hydrate, solvate or polymorph thereof in combination with the at least one further agent, or a pharmaceutically acceptable salt, hydrate, solvate or polymorph thereof.

13. The method according to claim 12, wherein the step of administering Afabicin, or a pharmaceutically acceptable salt, hydrate, solvate or polymorph thereof, in combination with the at least one further agent, or a pharmaceutically acceptable salt, hydrate, solvate or polymorph thereof, is carried out prior to and/or after the step of exchanging the medical implant.

14. The method according to claim 1, wherein the at least one further agent, or a pharmaceutically acceptable salt, hydrate, solvate or polymorph thereof, is administered orally, parenterally, transdermally, intravenously and/or topically.

15. The method according to claim 12, wherein the method includes a first step of removal of the medical implant, a second step of intravenous administration of Afabicin or a pharmaceutically acceptable salt, hydrate, solvate or polymorph thereof in combination with the at least one further agent, or a pharmaceutically acceptable salt, hydrate, solvate or polymorph thereof, a third step of introducing a new medical implant, a fourth step of intravenous administration of Afabicin or a pharmaceutically acceptable salt, hydrate, solvate or polymorph thereof in combination with the at least one further agent, or a pharmaceutically acceptable salt, hydrate, solvate or polymorph thereof, and a fifth step of oral administration of Afabicin or a pharmaceutically acceptable salt, hydrate, solvate or polymorph thereof in combination with the at least one further agent, or a pharmaceutically acceptable salt, hydrate, solvate or polymorph thereof.

16. The method according to claim 1, wherein the at least one further agent is selected from the group consisting of Daptomycin, Vancomycin, Surfactin, A54145, Amphomycin, Friulimicin, laspartomycin, WAP-8294A$_2$, Katanosin, Plusbacin A3, Oritavancin, Telavancin, Teicoplanin, Dalbavancin, Ramoplanin, Mannopeptimycin, Clindamycin, Lincomycin and Pirlimycin and/or a pharmaceutically acceptable salt, hydrate, solvate or polymorph of any of these agents.

17. The method according to claim 16, wherein the at least one further agent is Daptomycin or a pharmaceutically acceptable salt, hydrate, solvate or polymorph thereof and/or Vancomycin or a pharmaceutically acceptable salt, hydrate, solvate or polymorph thereof and/or Clindamycin or a pharmaceutically acceptable salt, hydrate, solvate or polymorph thereof.

18. The method of claim 1, wherein the lipopeptide is Daptomycin or a pharmaceutically acceptable salt, hydrate, solvate or polymorph thereof, the glycopeptide is Vancomycin or a pharmaceutically acceptable salt, hydrate, solvate or polymorph thereof, and the lincosamide is Clindamycin or a pharmaceutically acceptable salt, hydrate, solvate or polymorph thereof.

19. The method of claim 3, wherein the *staphylococcus* bacterium is *Staphylococcus aureus* and/or CONS.

20. The method of claim 4, wherein the bacterial infection is associated with an open wound.

21. The method of claim 5, wherein the Afabicin, or a pharmaceutically acceptable salt, hydrate, solvate or polymorph thereof, in combination with the at least one further agent, or pharmaceutically acceptable salt, hydrate, solvate or polymorph thereof, is administered pre and/or post operatively.

22. The method of claim 7, wherein the staphylococci is *Staphylococcus aureus* or a CONS.

23. The method of claim 9, wherein the medical implant is a prosthetic joint.

24. The method of claim 10, wherein the bacterial infection is selected from a catheter-associated infection, an infection associated with endotracheal tubes, an infection associated with voice prostheses, and an infection associated with soft tissue fillers wherein said soft tissue fillers can be permanent or semi-permanent.

25. The method of claim 13, wherein said administration is carried out prior to and after the step of exchanging the medical implant.

26. The method of claim 13, wherein the method includes a first step of removal of the medical implant, a second step of intravenous administration of Afabicin or a pharmaceutically acceptable salt, hydrate, solvate or polymorph thereof in combination with the at least one further agent or a pharmaceutically acceptable salt, hydrate, solvate or polymorph thereof, a third step of introducing a new medical implant, a fourth step of intravenous administration of Afabicin or a pharmaceutically acceptable salt, hydrate, solvate or polymorph thereof in combination with the at least one further agent or a pharmaceutically acceptable salt, hydrate, solvate or polymorph thereof, and a fifth step of oral administration of Afabicin or a pharmaceutically acceptable salt, hydrate, solvate or polymorph thereof in combination with the at least one further agent or a pharmaceutically acceptable salt, hydrate, solvate or polymorph thereof.

27. The method of claim 1, wherein the one further agent or pharmaceutically acceptable salt, hydrate, solvate or polymorph thereof is daptomycin or pharmaceutically acceptable salt, hydrate, solvate or polymorph thereof.

28. The method of claim 27, wherein the biofilm contains or consists of *staphylococcus* bacteria.

29. The method of claim 28, wherein the *staphylococcus* bacteria are selected from the group consisting of:
Staphylococcus aureus,
Coagulase negative Staphylococci (CoNS),
Methicillin-susceptible or methicillin-resistant Staphylococci,
Staphylococcus aureus strains, or CONS strains wherein said strains are resistant to one or more antibiotic, and
Multidrug resistant Staphylococcus strains.

30. The method according to claim 27, wherein the bacterial infection is selected from the group consisting of:
a medical implant associated infection,
osteomyelitis,
infections in cystic fibrosis patients,
pleuropulmonary infections,
endocarditis,
wound infections,
mastitis,
sinusitis,
otitis media,
urinary tract infections,
tonsillitis,
laryngitis,
infection associated with kidney stones
biliary tract infections,
aerobic vaginitis,
septic thrombophlebitis,
infections associated with intracellular biofilms, and
colonization by *Staphylococcus aureus* that predisposes the patient to infections.

31. The method according to claim 3, wherein:
the Staphylococcus aureus is community-acquired Staphylococcus aureus or hospital-acquired Staphylococcus aureus;
the Coagulase negative Staphylococci (CoNS) is *Staphylococcus epidermidis, Staphylococcus haemolyticus, Staphylococcus lugdunensis, Staphylococcus simulans*, or *Staphylococcus hominis;*
the Methicillin-susceptible or methicillin-resistant Staphylococcus is Staphylococcus aureus or Staphylococcus epidermidis;
the antibiotic is selected from β-lactams, Cephalosporins, Glycopeptides, Linezolid, Lincosamides, Rifampicin, Lipopeptides, Fluoroquinolones, Trimethoprim/Sulfamethoxazole, Fosfomycin, Fusidic acid, Tigecycline, Tetracyclines, and Dalbavancin; or
the Multidrug resistant *staphylococcus* strain is selected from the group consisting of Multidrug resistant Staphylococcus aureus strains and Multidrug resistant CONS strains.

32. The method according to claim 31, wherein the CoNS is *Staphylococcus epidermidis* or the Multidrug resistant CoNS strain is *Staphylococcus epidermidis*.

33. The method according to claim 31, wherein:
the Glycopeptide is Vancomycin;
the Lincosamide is Clindamycin; or
the Lipopeptide is Daptomycin.

34. The method according to claim 33, wherein the CoNS is *Staphylococcus epidermidis*.

35. The method according to claim 8, wherein:
the pleuropulmonary infection is chronic,
the endocarditis is native valve endocarditis,
the wound infections are chronic,
the sinusitis is chronic,
the otitis media is chronic,
the tonsillitis is chronic,
the laryngitis is chronic, or
the infections associated with intracellular biofilms are in Kupffer cells or in tonsillar cells.

36. The method according to claim 35, wherein the pleuropulmonary infection is obstructive pulmonary disease.

37. The method according to claim 29, wherein:
the *Staphylococcus aureus* is community-acquired *Staphylococcus aureus* or hospital-acquired *Staphylococcus aureus;*
the Coagulase negative Staphylococci (CoNS) is *Staphylococcus epidermidis, Staphylococcus haemolyticus, Staphylococcus lugdunensis, Staphylococcus simulans,* or *Staphylococcus hominis;*
the Methicillin-susceptible or methicillin-resistant *Staphylococcus* is *Staphylococcus aureus* or *Staphylococcus epidermidis;*
the antibiotic is selected from β-lactams, Cephalosporins, Glycopeptides, Linezolid, Lincosamides, Rifampicin, Lipopeptides, Fluoroquinolones, Trimethoprim/Sulfamethoxazole, Fosfomycin, Fusidic acid, Tigecycline, Tetracyclines, and Dalbavancin; or
the Multidrug resistant *staphylococcus* strain is selected from the group consisting of Multidrug resistant *Staphylococcus aureus* strains and Multidrug resistant CoNS strains.

38. The method according to claim 37, wherein the CoNS is *Staphylococcus epidermidis* or the Multidrug resistant CoNS strain is *Staphylococcus epidermidis*.

39. The method according to claim 37, wherein:
the Glycopeptide is Vancomycin;
the Lincosamide is Clindamycin; or
the Lipopeptide is Daptomycin.

40. The method according to claim 39, wherein the CoNS is *Staphylococcus epidermidis*.

41. The method according to claim 30, wherein:
the pleuropulmonary infection is chronic,
the endocarditis is native valve endocarditis,
the wound infections are chronic,
the sinusitis is chronic,
the otitis media is chronic,
the tonsillitis is chronic,
the laryngitis is chronic, or
the infections associated with intracellular biofilms are in Kupffer cells or in tonsillar cells.

42. The method according to claim 41, wherein the pleuropulmonary infection is obstructive pulmonary disease.

\* \* \* \* \*